(12) United States Patent
Huentelman et al.

(10) Patent No.: US 9,127,316 B2
(45) Date of Patent: Sep. 8, 2015

(54) MARKERS ASSOCIATED WITH ALZHEIMER'S DISEASE

(75) Inventors: Matt Huentelman, Phoenix, AZ (US); Eric M. Reiman, Scottsdale, AZ (US)

(73) Assignee: THE TRANSLATIONAL GENOMICS RESEARCH INSTITUTE, Phoenix, AZ (US)

( * ) Notice: Subject to any disclaimer, the term of this patent is extended or adjusted under 35 U.S.C. 154(b) by 391 days.

(21) Appl. No.: 13/046,580

(22) Filed: Mar. 11, 2011

(65) Prior Publication Data

US 2011/0263439 A1    Oct. 27, 2011

Related U.S. Application Data

(60) Provisional application No. 61/312,855, filed on Mar. 11, 2010.

(51) Int. Cl.
  *C12Q 1/68*  (2006.01)
  *C07H 21/04*  (2006.01)
  *C12M 3/00*  (2006.01)
  *G01N 33/68*  (2006.01)

(52) U.S. Cl.
  CPC .......... *C12Q 1/6883* (2013.01); *G01N 33/6896* (2013.01); *C12Q 2600/112* (2013.01); *C12Q 2600/156* (2013.01); *C12Q 2600/172* (2013.01)

(58) Field of Classification Search
  None
  See application file for complete search history.

(56) References Cited

U.S. PATENT DOCUMENTS

2008/0051318 A1 *  2/2008  Li et al. .............................. 514/2
2008/0286876 A1 * 11/2008  Stephanie ...................... 436/86

OTHER PUBLICATIONS

International Preliminary Report on Patentability for PCT application No. PCT/US11/028205 dated Sep. 11, 2012.
International Search Report and Written Opinion of Searching Authority for PCT application No. PCT/US11/028205 dated Feb. 17, 2012.
Groupe, A. et al. 'Evidence for novel susceptibility genes for late-onset Alzheimer's disease from a genome-wide association study of putative functional variants' Human Molecular Genetics. vol. 16(8), pp. 865-873 (Feb. 22, 2007) See the abstract.
Bizzarro, A. et al. 'The complex interaction between APOE promoter and AD: an Italian case-control study' European Journal of Human Genetics. vol. 17(7), pp. 938-945 (Jan. 28, 2009) See the abstract.
Figgins, J. A. et al. 'Association studies of 22 candidate SNPs with late-onset Alzheimer's disease' American Journal of Medical Genetics Part B. vol. 150B, pp. 520-526 (Jun. 5, 2009) See the abstract.
Xu, P. T. et al. A Sage study of apolipoprotein E3/3, E3/4 and E4/4 allele-specific gene expression in hippocampus in Alzheimer disease Molecular and Cellular Neuroscience. vol. 36(3), pp. 313-331 (Jul. 24, 2007) See the abstract.

* cited by examiner

*Primary Examiner* — Kenneth R. Horlick
*Assistant Examiner* — David Thomas

(57) ABSTRACT

This application discloses SNPs capable of predicting increased or decreased risk of developing late onset Alzheimer's disease.

19 Claims, No Drawings

SEQUENCE LISTING

```
<160> NUMBER OF SEQ ID NOS: 3

<210> SEQ ID NO 1
<211> LENGTH: 500
<212> TYPE: DNA
<213> ORGANISM: Homo sapiens
<220> FEATURE:
<221> NAME/KEY: misc_feature
<223> OTHER INFORMATION: R=A or G
```

```
<400> SEQUENCE: 1
aaagaaaggg gaaagaaaag gtatatttga aatggagaca tagcccaagg ctcttaaact        60
cagggttatg tcagtcatga tgtaataaaa tcatgaggcc ctacatatat tgtttttctc       120
cttttggtat aagcttgggt ttcagagcca tgttttcga cgccagtaaa acttccagca        180
ctagcatgga aatgaactgc agtcgatggc tgccctcaag gttggagagg ggataggaaa       240
ctggggctgc rttgaactgg acaacacttg tctggtctca ggtggatgac tggtgtcagc       300
ccagaatggc caggaggtgt ggcaagattt tcctgtttgc ctaaagaaag taaccacttg       360
ggatctcctg cttgtaaatg ttggcccmgt ttttgaactc tacaggggct aaagaaatca       420
tccccgagga ctgagttcag cttgtgggtc tccagcttgc gctctctgct gttcattgct       480
atagtcttgc aagaaggtgg                                                   500

<210> SEQ ID NO 2
<211> LENGTH: 52
<212> TYPE: DNA
<213> ORGANISM: Homo sapiens
<220> FEATURE:
<221> NAME/KEY: misc_feature
<223> OTHER INFORMATION: The "A" allele of rs17042395

<400> SEQUENCE: 2
gagaggggat aggaaactgg ggctgcattg aactggacaa cacttgtctg gt               52

<210> SEQ ID NO 3
<211> LENGTH: 51
<212> TYPE: DNA
<213> ORGANISM: Homo sapiens
<220> FEATURE:
<221> NAME/KEY: misc_feature
<223> OTHER INFORMATION: The "G" allele of rs17042395

<400> SEQUENCE: 3
gagaggggat aggaaactgg ggctgcgttg mctggacaac acttgtctgg t                51
```

MARKERS ASSOCIATED WITH ALZHEIMER'S DISEASE

CROSS-REFERENCE TO RELATED APPLICATIONS

This application claims the benefit under 35 USC 119(e) of U.S. Provisional Patent Application No. 61/312,855, filed Mar. 11, 2010, which is incorporated herein by reference in its entirety for all purposes.

SEQUENCE LISTING

This application contains a sequence listing in computer readable format, the teachings and content of which are hereby incorporated by reference.

FIELD

The present invention relates to genetic markers, compositions for the detection of genetic markers, and methods for assessing risk of developing Alzheimer's disease.

BACKGROUND

Disorders of the brain are serious medical conditions causing disability and diminished quality of life. Neurological damage is largely irreversible and thus early diagnosis and close monitoring are critical to the successful treatment of patients. Alzheimer's disease (AD) is a neurodegenerative disease associated with progressive memory loss and cognitive dysfunction. It is associated with abnormal clumps (amyloid plaques) and tangled bundles of fibers (neurofibrillary tangles) in the brain, both of which are considered signs of AD. An estimated 4 million Americans have AD. By the year 2030 approximately 1 in every 80 persons in the U.S. will have AD. Familial Alzheimer's disease (FAD) is known to be inherited. In affected families, members of at least two generations have had the disease. FAD is rare, accounting for less than 1% of all cases of AD. FAD has an earlier onset, i.e., about 40 years of age and can be observed to run in families.

Early-onset Alzheimer's disease (EOAD) is a rare form of Alzheimer's disease in which individuals are diagnosed with the disease before age 65. Less than 10% of all Alzheimer's disease patients have EOAD. Younger individuals who develop Alzheimer's disease exhibit more of the brain abnormalities that are normally associated with Alzheimer's disease. EOAD is usually familial and follows an autosomal dominant inheritance pattern. To date, mutations in three genes including amyloid precursor protein (APP) on chromosome 21, presenilin 1 (PSEN1) on chromosome 14 and presenilin 2 (PSEN2) on chromosome 1 have been identified in families with EOAD. Mutations in the APP, PSEN1 and PSEN2 genes account for about 50% of the disease. Most of the pathogenic mutations in the APP and presenilin genes are associated with abnormal processing of APP, which leads to the overproduction of toxic A~-1-42. Down syndrome patients, who have three copies of chromosome 21 which includes the APP gene, begin to develop the characteristic senile plaques and tau tangles at the ages of 30 and 40 (Kamboh, *Annals of Human Genetics* 68:381-404, 2004).

Late-onset Alzheimer's disease (LOAD) is the most common form of Alzheimer's disease, accounting for about 90% of cases and usually occurring after age 65. LOAD strikes almost half of all individuals over the age of 85 and may or may not be hereditary. It is a complex and multifactorial disease with the possible involvement of several genes. Genome-wide linkage or linkage disequilibrium studies on LOAD have provided informative data for the existence of multiple putative genes for AD on several chromosomes, with the strongest evidence on chromosomes 12, 10, 9 and 6. LOAD cases tend to be sporadic, wherein there is no family history of the disease. Genetic susceptibility at multiple genes and interaction between these genes as well as environmental factors are most likely responsible for the etiology of LOAD. Twin data on incident cases indicates that almost 80% of the LOAD risk is attributable to genetic factors. The Apolipoprotein E (APOE) gene on chromosome 19q13 has been identified as a strong risk factor for LOAD. In fact, the APOE-$\epsilon$4 allele has been established as a strong susceptibility marker that accounts for nearly 30% of the risk in late-onset AD. More specifically, three variants of APOE, encoded by codons 112 and 158, have been found to modify the risk of LOAD. As compared to the common APOE-$\epsilon$3 allele (codon 112=Cys and codon 158=Arg), the APOE-$\epsilon$4 allele (codon 112=Arg and codon 158=Arg) increases the risk of AD, while the APOE-$\epsilon$2 allele (codon 112=Cys and codon 158=Cys) decreases the risk of AD. The effect of the APOE-$\epsilon$4 allele is dose related, wherein one or two copies of the APOE-$\epsilon$4 allele are associated with 3-fold or 15-fold risk, respectively. However, the effect of the APOE-$\epsilon$4 allele on AD risk appears to decline with increasing age (Kamboh, 2004, supra).

From the time of diagnosis, people with AD survive about half as long as those of similar age without dementia. Medicare costs for beneficiaries with AD were $91 billion in 2005 and may increase to as much as $160 billion in 2010. Finding a treatment that could delay the onset by five years could reduce the number of individuals with AD by nearly 50 percent after 50 years. Drug development for AD is very active and sensitive diagnostic and screening technologies could identify patients for therapy and monitor their response. Improved diagnostic tools for AD would thus be a significant advancement to drug development for this disease and would also provide a way to guide therapeutic decision making thus improving outcomes and reducing unnecessary exposure of patients to costly medications with unwanted side effects.

SUMMARY

The present invention relates to genetic markers, compositions for the detection of genetic markers, and methods for assessing risk of developing Alzheimer's disease.

In particular, the present invention provides methods of classifying a subject to a late onset Alzheimer's disease risk group, comprising: receiving a sample from the subject; detecting a marker in Table 2; and classifying the subject into a risk group based upon the presence or absence of the marker. In some embodiments, the methods further comprising isolating nucleic acid from the sample. In some embodiments, the marker is detected directly. In some of these embodiments, the marker detection comprises a method selected from the group consisting of Sanger sequencing, pyrosequencing, SOLID sequencing, massively parallel sequencing, barcoded DNA sequencing, PCR, real-time PCR, quantitative PCR, microarray analysis of genomic DNA with a gene chip, restriction fragment length polymorphism analysis, allele specific ligation, and comparative genomic hybridization. In other embodiments, the marker is detected indirectly. In some of these embodiments, the marker detection comprises a method selected from the group consisting of microarray analysis of RNA, RNA in situ hybridization, RNAse protection assay, Northern blot, reverse transcriptase PCR, quantitative PCR, quantitative reverse transcriptase PCR, quantitative real-time reverse transcriptase PCR, reverse transcriptase treatment followed by direct sequencing, flow cytometry, immunohistochemistry, ELISA, Western blot, immunoaffinity chromatograpy, HPLC, mass spectrometry, protein microarray analysis, PAGE analysis, isoelectric focusing, and 2-D gel electrophoresis. In some embodiments, the marker is associated with a high risk of developing LOAD and the subject is classified to a risk group with high risk of LOAD if the marker is detected in the sample. In a subset of these embodiments, the subject is further classified based on the presence or absence of the APOE-ε4 allele. In some embodiments, the marker is associated with a low risk of developing LOAD and the subject is classified to a risk group with low risk of LOAD if the marker is detected in the sample. In a subset of these embodiments, the marker is the A allele of rs17042395. In some embodiments, the subject is further classified based on the presence of two copies of the APOE-e3 allele.

In addition, the present invention provides sets of molecular probes used in assessing the risk of developing late onset Alzheimer's disease (LOAD) comprising: a first probe capable of detecting a first SNP selected from Table 2; and a second probe capable of detecting a second SNP selected from Table 2; wherein the probes are associated with a microarray of 1000 or fewer elements. In some embodiments, the first probe is capable of detecting a SNP associated with a higher risk of developing LOAD. In some embodiments, the second probe is capable of detecting a SNP associated with a lower risk of developing AD. In other embodiments, the first probe and the second probe are capable of detecting a SNP associated with a lower risk of developing LOAD. In some preferred embodiments, the first probe detects the A allele of rs17042395 and the second probe detects the apoe3 allele.

Moreover, the present invention provides methods of classifying a subject to a late onset Alzheimer's disease (LOAD) risk group, comprising: receiving a sample from the subject; detecting an A allele of rs17042395; detecting an E3 allele of APOE; and classifying the subject in a low LOAD risk group if both the A allele of rs17042395 and the E3 allele of APOE are detected. In some embodiments, the methods further comprise isolating nucleic acid from the sample. In some embodiments, the marker is detected directly. In some of these embodiments, the marker detection comprises a method selected from the group consisting of Sanger sequencing, pyrosequencing, SOLID sequencing, massively parallel sequencing, barcoded DNA sequencing, PCR, real-time PCR, quantitative PCR, microarray analysis of genomic DNA with a gene chip, restriction fragment length polymorphism analysis, allele specific ligation, and comparative genomic hybridization. In some embodiments, the marker is detected indirectly. In some of these embodiments, the marker detection comprises a method selected from the group consisting of microarray analysis of RNA, RNA in situ hybridization, RNAse protection assay, Northern blot, reverse transcriptase PCR, quantitative PCR, quantitative reverse transcriptase PCR, quantitative real-time reverse transcriptase PCR, reverse transcriptase treatment followed by direct sequencing, flow cytometry, immunohistochemistry, ELISA, Western blot, immunoaffinity chromatograpy, HPLC, mass spectrometry, protein microarray analysis, PAGE analysis, isoelectric focusing, and 2-D gel electrophoresis.

DETAILED DESCRIPTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention.

Aspects and applications of the invention presented here are described below in the drawings and detailed description of the invention. Unless specifically noted, it is intended that the words and phrases in the specification and the claims be given their plain, ordinary, and accustomed meaning to those of ordinary skill in the applicable arts.

If a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that the noun, term, or phrase is given its broadest possible meaning.

The use of the words "function," "means" or "step" herein is not intended to somehow indicate a desire to invoke the special provisions of 35 U.S.C. §112, ¶6, to define the invention. To the contrary, if the provisions of 35 U.S.C. §112, ¶6 are sought to be invoked to define the inventions, the claims will specifically and expressly state the exact phrases "means for" or "step for, and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then the provisions of 35 U.S.C. §112, ¶6 are not invoked. Moreover, even if the provisions of 35 U.S.C. §112, ¶6 are invoked to define the claimed inventions, it is intended that the inventions not be limited only to the specific structure, material or acts that are described in the preferred embodiments, but in addition, include any and all structures, materials or acts that perform the claimed function as described in alternative embodiments or forms of the invention, or that are well known present or later-developed, equivalent structures, material or acts for performing the claimed function.

Alzheimer's disease (AD) is a progressive neurodegenerative disorder characterized by memory and cognitive impairments and other non-cognitive behavioral symptoms. Age is the strongest risk factor, wherein almost 50% of people over the age of 85 are affected. Early onset AD (EOAD) is associated with genetic mutations in amyloid precursor protein (APP), presenilin I (PSENI) and presenilin 2 (PSEN2). However, sporadic or late-onset AD (LOAD) is multi-factorial and genetically more complex. In addition, genetic factors may account for as much as 80% of the disease risk associated with LOAD (Gatz et al. (2006) Arch. Gen. Psychiatry 63(2):168-174). While monogenic mutations cause EOAD, the only extensively validated susceptibility gene for LOAD is the apolipoprotein E (APOE-e4) allele (Saunders et al. (1993) *Neurology* 43(8):1467-1472 and Farrer et al. (1997) *JAMA* 278(16): 1349-1356). But alleles of the APOE gene do not account for all of the genetic load responsible for LOAD predisposition. Stratification by APOE-ε4 carrier status allows for the detection of association signals that are normally overwhelmed and thus, masked by the signal of APOE alleles in a non-stratified study design.

AD is the most common cause of disabling memory and thinking problems in older persons. According to one study, it afflicts about 10% of those over the age of 65 and almost half of those over the age of 85. According to another study, the prevalence of the disorder increases from 1% by the age of 60 years to 40% in nonagenarians (See Reference 1). By 2050, the number of afflicted persons is projected to quadruple, leading to ~16 million patients and a cost of more than $750 billion per year (with no adjustment for inflation) in the United States alone. Meantime, the disorder takes a devastating toll on patients and their families. Clinically, AD is characterized by gradual but progressive declines in memory, language skills, ability to recognize objects or familiar faces, ability to perform routine tasks, and judgment and reasoning. Associated features commonly include agitation, paranoid delusions, sleepiness, aggressive behaviors, and wandering. In its most severe form, patients may be confused, bed-ridden, unable to control their bladder or bowel functions, or swallow. By contributing to other problems (e.g., inanition and infections), it is considered the fourth leading cause of death in the United States. Neuropathologically, AD is characterized by the accumulation of neuritic plaques (the major component of which is the amyloid-B peptide [Aβ], neurofibrillary tangles (NFT, the major component of which is the hyper-phosphorylated form of the protein tau). While the etiology leading to the development of AD has not been clearly resolved, genetic factors play a major role.

Twin studies report a higher concordance of AD among monozygotic compared to dizygotic twins, with heritability estimates between 60% and 80% (See Reference 2). Some rare forms of the disease (<1% by some estimates) are caused by more than 200 mutations in the genes encoding the amyloid precursor protein (APP), presenilin I (PSI) and presenilin 2 (PS2). These mutations, which influence directly the production of Aβ, cause a form of AD characterized by autosomal dominant inheritance and an early age of dementia onset (typically before the age of 60). However, the majority of AD cases are not dominantly inherited and there is a broad consensus that AD is genetically complex and heterogeneous and that genetic polymorphisms contribute substantially to the risk of disease.

The ε4 allele of the apolipoprotein E (APOE) genotype is the only well-established genetic susceptibility factor for sporadic or familial AD (See Reference 4). While subsequent association studies have suggested the existence of additional AD susceptibility genes, most of the results have not been replicated consistently. A variety of approaches, each with its strengths and limitations, are being taken in an attempt to discover additional AD susceptibility genes. One approach is the use of genome-wide scans.

Large case-control association studies are one approach being to identify genes that predispose to genetically complex neuropsychiatric disorders (See Reference 8). In AD, the candidate-gene approach has been mostly used in case-control association studies because it is straightforward and because it uses information generated in previous epidemiologic studies or laboratory experiments. The development of dense, genome-wide genotyping technologies such as the 100 k and 500 k SNP genotyping chips by Affymetrix allowed, for the first time, a hypothesis-free approach in the genetics of such complex diseases as AD. Reiman et al. previously applied this approach to a set of 1,411 samples that included 1,044 post-mortem neuropathologically verified cases and controls. After multiple testing corrections, the only locus that remained significant in the whole genome screen was APOE (See Reference 9).

Based on the hypothesis that the signal from APOE could be overwhelming other significantly associated loci, the cohort was stratified into those who were carriers of the APOE-ε4 risk allele and those who were non-carriers and the analysis was repeated in these subgroups. Among those who were carriers of APOE-ε4, a significant association was detected between AD and the Grb-2 associated binding protein (GAB2) (See Reference 10). Set association analysis also produced a set of 5 SNPs that improved genetic risk assessment of late onset AD, particularly for those who were not carriers of the APOE-ε4 risk allele.

In people with AD, changes in the brain may begin 10 to 20 years before any visible signs or symptoms appear. Some regions of the brain may begin to shrink, resulting in memory loss, the first visible sign of AD. Over time, AD progresses through three main stages: mild, moderate, and severe. These stages are characterized by a collection of signs and symptoms and behaviors that individuals with AD experience. People with mild symptoms of AD often seem healthy, but they are actually having difficulty making sense of the world around them. Initial symptoms are often confused with changes that take place in normal aging. Symptoms and early signs of AD may include difficulty learning and remembering new information, difficulty managing finances, planning meals, taking medication on schedule, depression symptoms (sadness, decreased interest in usual activities, loss of energy), getting lost in familiar places, etc. In moderate AD, the damaging processes occurring in the brain worsen and spread to other areas that control language, reasoning, sensory processing, and thought. In this stage, symptoms and signs of AD become more pronounced and behavioral problems may become more obvious. Signs and symptoms of moderate AD may include forgetting old facts, repeating stories and/or questions over and over, making up stories to fill gaps, difficulty performing tasks, following written notes, agitation, restlessness, repetitive movements, wandering, paranoia, delusions, hallucinations, deficits in intellect and reasoning, lack of concern for appearance, hygiene, and sleep, etc. In the advanced stage of AD, damage to the brain's nerve cells is widespread. At this point, full-time care is typically required. People with severe AD may have difficulty walking, and they often suffer complications from other illnesses, such as pneumonia. Signs of severe AD may include screaming, mumbling, speaking gibberish, refusing to eat, failing to recognize family or faces, and difficulty with all essential activities of daily living.

A single polynucleotide polymorphism (or SNP) may be any DNA sequence variation that involves a change in a single nucleotide.

A haplotype may be any combination of one or more closely linked alleles inherited as a unit. Different combinations of polymorphisms may also be called haplotypes. The difference of a single genetic marker can delineate a distinct haplotype. Alternatively, the results from several loci could be referred to as a haplotype. For example, a haplotype can be a set of SNPs on a single chromatid that are statistically associated to be likely to be inherited as a unit. Two or more alleles likely to be inherited as a unit may be termed a haplotype block. The haplotype block may, in turn, be used to identify other polymorphic sites in its region. Upon identification of a haplotype block associated with a particular haplotype, one of skill in the art may readily identify all other DNA polymorphisms associated with the particular haplotype by routine sequencing of the genomic DNA of an individual having such haplotype (such as an individual homozygous for such haplotype).

An allele includes any form of a particular nucleic acid that may be recognized as a form of the particular nucleic acid on account of its location, sequence, or any other characteristic. Alleles include but need not be limited to forms of a gene that include point mutations, silent mutations, deletions, frameshift mutations, single nucleotide polymorphisms (SNPs), inversions, translocations, heterochromatic insertions, and differentially methylated sequences relative to a reference gene, whether alone or in combination. The presence or absence of an allele may be detected through the use of any process through which a specific nucleic acid molecule may be detected, including direct and indirect methods of detecting the presence or absence of an allele. An allele may occur in a non-coding or coding region of a genome. If it is in a coding region, it may affect a particular triplet codon. If the allele does affect the codon, it may change the amino acid in the protein resulting from expression of the allele. An exception is if the allele is a silent mutation. In that case, the allele is a mutation in the coding region that does not change the amino acid that the codon encodes. An allele may also be called a mutation or a mutant. An allele may be compared to another allele that may be termed a wild type form of an allele. In some cases, the wild type allele is more common than the mutant.

When a SNP haplotype block is identified by a SEQ ID NO, a set of at least two SNPs that are associated with an allele of a gene are grouped together in the form of a synthetic nucleotide sequence. Detecting the SNPs in a given haplotype block in a subject may be associated with a greater or lesser risk that the subject will develop LOAD. A nucleic acid may be termed to be specific to a SNP haplotype block or specific to a SNP within a haplotype block. A nucleic acid specific to a haplotype block or a SNP within a haplotype block contains sequence that is complementary to at least one SNP that is grouped within that haplotype block. Such nucleic acids may be complementary to a SNP that is associated with the synthetic nucleotide sequence or any other SNP associated within the haplotype identified by the SNP haplotype block.

The HapMap is a catalog of common genetic variants that occur in human beings. It describes what these variants are, where they occur in the DNA, and how they are distributed among individuals within populations and among populations in different parts of the world (See the following reference: A haplotype map of the human genome (2005) *Nature* 437:1299-1320).

A marker may be any molecular structure produced by a cell, expressed inside the cell, accessible on the cell surface, or secreted by the cell. A marker may be any protein, carbohydrate, fat, nucleic acid, catalytic site, or any combination of these such as an enzyme, glycoprotein, cell membrane, virus, cell, organ, organelle, or any uni- or multimolecular structure or any other such structure now known or yet to be disclosed whether alone or in combination. A marker may also be called a target and the terms are used interchangeably.

A marker may be represented by the sequence of a nucleic acid from which it can be derived or any other chemical structure. Examples of such nucleic acids include miRNA, tRNA, siRNA, mRNA, cDNA, or genomic DNA sequences including complimentary sequences. Alternatively, a marker may be represented by a protein sequence. The concept of a marker is not limited to the products of the exact nucleic acid sequence or protein sequence by which it may be represented. Rather, a marker encompasses all molecules that may be detected by a method of assessing the expression of the marker.

Examples of molecules encompassed by a marker represented by a particular sequence or structure include point mutations, silent mutations, deletions, frameshift mutations, translocations, alternative splicing derivatives, differentially methylated sequences, differentially modified protein sequences, truncations, soluble forms of cell membrane associated markers, and any other variation that results in a product that may be identified as the marker. The following non-limiting examples are included for the purposes of clarifying this concept: If expression of a specific marker in a sample is assessed by RTPCR, and if the sample expresses an mRNA sequence different from the sequence used to identify the specific marker by one or more nucleotides, but the marker may still be detected using RTPCR, then the specific marker encompasses the sequence present in the sample. Alternatively if expression of a specific marker in a sample is assessed by an antibody and the amino acid sequence of the marker in the sample differs from a sequence used to identify marker by one or more amino acids, but the antibody is still able to bind to the version of the marker in the sample, then the specific marker encompasses the sequence present in the sample.

The genetic sequences of different individuals are remarkably similar. When the chromosomes of two humans are compared, their DNA sequences can be identical for hundreds of bases. But at about one in every 1000 to 1,200 bases, on average, the sequences will differ. As such, one individual might have an A at that location, while another individual has a G, or a person might have extra bases at a given location or a missing segment of DNA. Differences in individual bases are the most common type of genetic variation. These genetic differences are known as single nucleotide polymorphisms (SNPs) (supra). SNPs act as markers to locate genes in DNA. Given the relatively close spacing between these SNPs, SNPs are typically inherited in blocks.

The invention provides a method of assigning a subject to a late onset Alzheimer's disease (LOAD) risk group in order to assess the likelihood of the subject being afflicted with the disease. This method can be employed to assess the risk at early stages of disease progression. The method includes providing a biological sample from the subject, detecting a marker in a biological sample, which can be a haplotype associated with LOAD and assigning the subject to the late onset Alzheimer's disease (LOAD) risk group based upon the presence or absence of the haplotype. The method involves directly or indirectly detecting the presence or absence of the markers. In addition, the subject may be further stratified by LOAD risk group based upon whether the subject carries an apolipoprotein E allele associated with increased or altered LOAD risk. By way of example, APOE-ε4 is commonly associated with LOAD. In addition, various haplotypes of APOE have been associated with LOAD risk groups as set forth in U.S. Patent Publ. 2005/0277129. Finally multiple markers disclosed herein may be used in combination to improve the accuracy, preferably two or more, three or more, four or more, five or more, or ten or more of the markers may be used.

The invention contemplates that markers may be detected by a variety of methodologies or procedures that are well know in the art including, but not limited to, nucleic acid hybridization, antibody binding, activity assay, polymerase chain reaction (PCR), SI nuclease assay and via gene chip or microarray as well as any other assay known in the art that may be used to detect the SNPs associated with a haplotype or the gene product produced from the gene of the haplotype including mRNA and protein. Hybridization of a SNP-specific oligonucleotide to a target polynucleotide may be performed with both entities in solution, or such hybridization may be performed when either the oligonucleotide or the target polynucleotide is covalently or noncovalently affixed to a solid support. Attachment may be mediated, for example, by antibody-antigen interactions, poly-L-Lys, streptavidin or avidin-biotin interactions, salt bridges, hydrophobic interactions, chemical linkages, UV cross-linking baking, etc. SNP-specific oligonucleotides may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the SNP-specific oligonucleotide or target nucleic acid. Detecting the nucleotide or nucleotide pair of interest may also be determined using a mismatch detection technique, including but not limited to the RNase protection method using riboprobes (Winter et al. (1985) *Proc. Natl. Acad. Sci. USA* 82:7575; Meyers et al. (1985) Science 230: 1242) and proteins which recognize nucleotide mismatches, such as the *E. coli* mutS protein (Modrich (1991) *Ann. Rev. Genet.* 25:229-53). Alternatively, variant SNPs or variant alleles can be identified by single strand conformation polymorphism (SSCP) analysis (Orita et at. (1989) *Genomics* 5:874-9); Humphries et al. (1996) in MOLECULAR DIAGNOSIS OF GENETIC DISEASES, Elles, ed., pp. 321-340) or denaturing gradient gel electrophoresis (DGGE) (Wartell et al. (1990) *Nucl. Acids Res.* 18:2699706); Sheffield et al. (1989) *Proc. Natl. Acad. Sci. USA* 86:232-6). A polymerase-mediated primer extension method may also be used to identify the polymorphism(s). Several such methods have been described in the patent and scientific literature and include the "Genetic Bit Analysis" method (WO 92/15712) and the ligase/polymerase mediated genetic bit analysis (U.S. Pat. No. 5,679,524. Related methods are disclosed in WO 91102087, WO 90/09455, WO 95/17676, and U.S. Pat. Nos. 5,302,509 and 5,945,283. Extended primers containing the complement of the polymorphism may be detected by mass spectrometry as described in U.S. Pat. No. 5,605,798. Another primer extension method is allele-specific PCR (Ruano et al. (1989) *Nucl. Acids Res.* 17:8392; Ruano et al. (1991) *Nucl. Acids Res.* 19:6877-82); WO 93/22456; Turki et al. (1995) 1. *Clin. Invest.* 95:1635-41). The haplotype for a gene of an individual may also be determined by hybridization of a nucleic acid sample containing one or both copies of the gene, mRNA, cDNA or fragment(s) thereof, to nucleic acid arrays and sub-arrays such as described in WO 95/112995. The arrays would contain a battery of SNP-specific or allele specific oligonucleotides representing each of the polymorphic sites to be included in the haplotype.

Detecting the presence or absence of a marker disclosed herein or a close isoform thereof may be carried out either directly or indirectly by any suitable methodology. A variety of techniques are known to those skilled in the art (supra). All generally involve receiving a biological sample containing DNA or protein from the subject, and then detecting whether or not the marker or a close isoform thereof is present in the sample. and then determining the presence or absence of the marker in the sample.

The sample may be any type of sample derived from the subject, including any fluid or tissue that may contain one or more markers associated with the haplotype. Examples of sources of samples include but are not limited to biopsy or other in vivo or ex vivo analysis of prostate, breast, skin, muscle, fascia, brain, endometrium, lung, head and neck, pancreas, small intestine, blood, liver, testes, ovaries, colon, skin, stomach, esophagus, spleen, lymph node, bone marrow, kidney, placenta, or fetus. In some aspects of the invention, the sample comprises a fluid sample, such as peripheral blood, lymph fluid, ascites, serous fluid, pleural effusion, sputum, cerebrospinal fluid, amniotic fluid, lacrimal fluid, stool, or urine.

The marker may be detected by any of a number of methods. Direct methods of detecting the presence of an allele include but are not limited to any form of DNA sequencing including Sanger, next generation sequencing, pyrosequencing, SOLID sequencing, massively parallel sequencing, pooled, and barcoded DNA sequencing or any other sequencing method now known or yet to be disclosed; PCR-based methods such as real-time PCR, quantitative PCR, reverse transcription PCR or any combination of these; allele specific ligation; comparative genomic hybridization; or any other method that allows the detection of a particular nucleic acid sequence within a sample or enables the differentiation of one nucleic acid from another nucleic acid that differs from the first nucleic acid by one or more nucleotides. A sample may be from a subject suspected of having AD. Nucleic acids may include but need not be limited to RNA, cDNA, tRNA, mitochondrial DNA, plasmid DNA, siRNA, genomic DNA, or any other naturally occurring or artificial nucleic acid molecule. A subject may be any organism that may be subject to degenerative neurological diseases including mammals, further including humans.

In Sanger Sequencing, a single-stranded DNA template, a primer, a DNA polymerase, \nucleotides and a label such as a radioactive label conjugated with the nucleotide base or a fluorescent label conjugated to the primer, and one chain terminator base comprising a dideoxynucleotide (ddATP, ddGTP, ddCTP, or ddTTP, are added to each of four reaction (one reaction for each of the chain terminator bases). The sequence may be determined by electrophoresis of the resulting strands. In dye terminator sequencing, each of the chain termination bases is labeled with a fluorescent label of a different wavelength which allows the sequencing to be performed in a single reaction.

In pyrosequencing, the addition of a base to a single stranded template to be sequenced by a polymerase results in the release of a phyrophosphate upon nucleotide incorporation. An ATP sulfyrlase enayme converts pyrophosphate into ATP which in turn catalyzes the conversion of luciferin to oxyluciferin which results in the generation of visible light that is then detected by a camera.

In SOLID sequencing, the molecule to be sequenced is fragmented and used to prepare a population of clonal magnetic beads (in which each bead is conjugated to a plurality of copies of a single fragment) with an adaptor sequence and alternatively a barcode sequence. The beads are bound to a glass surface. Sequencing is then performed through 2-base encoding.

In massively parallel sequencing, randomly fragmented targeted DNA is attached to a surface. The fragments are extended and bridge amplified to create a flow cell with clusters, each with a plurality of copies of a single fragment sequence. The templates are sequenced by synthesizing the fragments in parallel. Bases are indicated by the release of a fluorescent dye correlating to the addition of the particular base to the fragment.

Examples of indirect methods of detection include any nucleic acid detection method including the following non-limiting examples, microarray analysis, RNA in situ hybridization, RNAse protection assay, Northern blot, reverse transcriptase PCR, quantitative PCR, quantitative reverse transcriptase PCR, quantitative real-time reverse transcriptase PCR, reverse transcriptase treatment followed by direct sequencing, direct sequencing of genomic DNA, or any other method of detecting a specific nucleic acid now known or yet to be disclosed. Other examples include any process of assessing protein expression including flow cytometry, immunohistochemistry, ELISA, Western blot, and immunoaffinity chromatograpy, HPLC, mass spectrometry, protein microarray analysis, PAGE analysis, isoelectric focusing, 2-D gel electrophoresis, or any enzymatic assay.

Other methods used to assess expression include the use of natural or artificial ligands capable of specifically binding a marker. Such ligands include antibodies, antibody complexes, conjugates, natural ligands, small molecules, nanoparticles, or any other molecular entity capable of specific binding to a marker. Antibodies may be monoclonal, polyclonal, or any antibody fragment including an Fab, $F(ab)_2$, Fv, scFv, phage display antibody, peptibody, multispecific ligand, or any other reagent with specific binding to a marker. Ligands may be associated with a label such as a radioactive isotope or chelate thereof, dye (fluorescent or nonfluorescent) stain, enzyme, metal, or any other substance capable of aiding a machine or a human eye from differentiating a cell expressing a marker from a cell not expressing a marker. Additionally, expression may be assessed by monomeric or multimeric ligands associated with substances capable of killing the cell. Such substances include protein or small molecule toxins, cytokines, pro-apoptotic substances, pore forming substances, radioactive isotopes, or any other substance capable of killing a cell.

Other markers may also be used that are associated with the markers disclosed herein such as SNPs or other polymorphic markers that are in close enough proximity to have a statistically significant association with the marker disclosed herein (i.e., other markers in linkage disequilibrium with a marker disclosed herein). For example, if a marker or a close isoform thereof is detected in the subject, then the subject may be placed into a group either at higher or lower risk for LOAD depending on which marker or close isoform thereof is identified (i.e., a significant enough number of markers associated with a haplotype).

The invention also provides set of molecular probes for detection, including at least two probes capable of detecting, directly or indirectly, a marker disclosed herein associated with increased or decreased risk of LOAD, wherein the molecular probes are not associated with a microarray of greater than 1000 elements, a microarray with greater than 500 elements, a microarray with greater than 100 elements, a microarray with greater than 50 elements, or are not associated with a microarray. Such sets of two or more probes may include at least one probe capable of detecting, directly or indirectly, a marker disclosed herein associated with higher risk of developing LOAD and at least one other probe is capable of detecting, directly or indirectly, a marker disclosed herein associated with lower risk of developing LOAD.

The expression of the marker in a sample may be compared to a level of expression predetermined to predict the presence or absence of a particular physiological characteristic. The level of expression may be derived from a single control or a set of controls. A control may be any sample with a previously determined level of expression. A control may comprise material within the sample or material from sources other than the sample. Alternatively, the expression of a marker in a sample may be compared to a control that has a level of expression predetermined to signal or not signal a cellular or physiological characteristic. This level of expression may be derived from a single source of material including the sample itself or from a set of sources. Comparison of the expression of the marker in the sample to a particular level of expression results in a prediction that the sample exhibits or does not exhibit the cellular or physiological characteristic.

Prediction of a cellular or physiological characteristic includes the prediction of any cellular or physiological state that may be predicted by assessing the expression of a marker. Examples include the identity of a cell as a particular cell including a particular normal or diseased cell type, the likelihood that one or more diseases is present or absent, the likelihood that a present disease will progress, remain unchanged, or regress, the likelihood that a disease will respond or not respond to a particular therapy, or any other disease outcome. Further examples include the likelihood that a cell will move, senesce, apoptose, differentiate, metastasize, or change from any state to any other state or maintain its current state.

One type of cellular or physiological characteristic is the risk that a particular disease outcome will occur. Assessing this risk includes the performing of any type of test, assay, examination, result, readout, or interpretation that correlates with an increased or decreased probability that an individual has had, currently has, or will develop a particular disease, disorder, symptom, syndrome, or any condition related to health or bodily state. Examples of disease outcomes include, but need not be limited to survival, death, progression of existing disease, remission of existing disease, initiation of onset of a disease in an otherwise disease-free subject, or the continued lack of disease in a subject in which there has been a remission of disease. Assessing the risk of a particular disease encompasses diagnosis in which the type of disease afflicting a subject is determined. Assessing the risk of a disease outcome also encompasses the concept of prognosis. A prognosis may be any assessment of the risk of disease outcome in an individual in which a particular disease has been diagnosed. Assessing the risk further encompasses prediction of therapeutic response in which a treatment regimen is chosen based on the assessment. Assessing the risk also encompasses a prediction of overall survival after diagnosis.

Determining whether or not the presence of an allele signifies a physiological or cellular characteristic may be assessed by any of a number of methods. The skilled artisan will understand that numerous methods may be used to select a marker or a plurality of markers that signifies a particular physiological or cellular characteristic. In diagnosing the presence of a disease, a threshold value may be obtained by performing the assay method on samples obtained from a population of patients having a certain type of disease (Alzheimer's disease for example,) and from a second population of subjects that do not have the disease. In assessing disease outcome or the effect of treatment, a population of patients, all of which may develop a disease such as AD, may be followed for a period of time. After the period of time expires, the population may be divided into two or more groups. For example, the population may be divided into a first group of patients who did develop AD and a second group of patients who did not develop AD. Examples of endpoints include occurrence of one or more symptoms of disease, death, formation of neurofibrillary tangles, memory loss, or other states to which the given disease may progress. If presence of the marker in a sample statistically aligns with one group relative to the other group, the subject from which the sample was derived may be assigned a risk of having the same outcome as the patient group that differentially displays the marker.

Other methods may be used to assess how accurately the presence or absence of a marker signifies a particular physiological or cellular characteristic. Such methods include a positive likelihood ratio, negative likelihood ratio, odds ratio, and/or hazard ratio. In the case of a likelihood ratio, the likelihood that the presence or absence of the marker would be found in a sample with a particular cellular or physiological characteristic is compared with the likelihood that the presence or absence of the marker would be found in a sample lacking the particular cellular or physiological characteristic.

An odds ratio measures effect size and describes the amount of association or non-independence between two groups. An odds ratio is the ratio of the odds of a marker being present or absent in one set of samples versus the odds of the marker being present or absent in the other set of samples. An odds ratio of 1 indicates that the event or condition is equally likely to occur in both groups. An odds ratio grater or less than 1 indicates that presence or absence of the marker is more likely to occur in one group or the other depending on how the odds ratio calculation was set up.

A hazard ratio may be calculated by estimate of relative risk. Relative risk is the chance that a particular event will take place. It is a ratio of the probability that an event such as development or progression of a disease will occur in samples in which a particular marker is present over the probability that the event will occur in samples in which the particular marker is absent. Alternatively, a hazard ratio may be calculated by the limit of the number of events per unit time divided by the number at risk as the time interval decreases. In the case of a hazard ratio, a value of 1 indicates that the relative risk is equal in both the first and second groups; a value greater or less than 1 indicates that the risk is greater in one group or another, depending on the inputs into the calculation.

Detection of the disease also includes detection of the haplotype by any SNPs/markers within the haplotype, but also indirectly through SNPs/markers outside the haplotype and leveraging linkage disequilibrium to identify carriers of the haplotype. In addition to determining a patient's relative risk for LOAD, the diagnosis may include prescribing therapeutic regimens to treat, prevent or delay onset of LOAD.

The method of diagnosis will further include direct or indirect detection of APOE alleles associated with LOAD, preferably the APOE-ε4 allele. Such detection may be performed using any of the detection methods available to one of skill in the art and the markers disclosed herein and APOE alleles may be detected using the same or different methods and may be detected at the same or different times. Further, the method of diagnosis may rely upon the information regarding the APOE alleles of the subject that had been previously determined. With information regarding any marker disclosed herein and APOE alleles of a subject, the diagnosis of risk may be determined and present in the form of Odds Ratio (OR) or other estimates for the set of alleles possessed by the subject.

EXAMPLES

Elements and acts in the example are intended to illustrate the invention for the sake of simplicity and have not necessarily been rendered according to any particular sequence or embodiment.

Example 1

Identification of SNPs Associated with LOAD

Only 46% of haplotypic variation from the CEPH population of the human HapMap may be captured by the Affymetrix 500K Mapping Assay. As a result, discoverable odds ratios in this study ranged from 2.0 to as low as 1.1-1.3. Use of discoverable odds ratios in this range require a study with greater statistical power, and in turn larger sample sizes. As a result, a genome-wide association study was performed that uses the Affymetrix 6.0 Array which measures ~906,000 SNPs (representing 85-95% genomic coverage) and ~946,000 copy number variations (CNVs), with a discovery cohort of over 2900 samples.

Generally, this type of study presents challenges due to biologic and phenotypic heterogeneity. The pathology of AD may present as a dementia syndrome, as MCI, or be present in persons without cognitive impairment. Additionally, Alzheimer's dementia is frequently due to a combination of AD pathology in addition to other common age-related pathlogies (e.g., cerebral infarctions). A typical approach to this problem is to create large sample sizes in order to detect a small signal from background heterogeneity. Along with the large sample size, this study used neuropathologically verified cases and controls to further control heterogeneity. This study also used quantitative endophenotypes that capture the range of clinical status (e.g., level of and change in cognitive function) and the spectrum of neuropathology (e.g., quantitative measures of AD pathology). Thus, two of the additional cohorts used herein are longitudinal, epidemiologic clinical pathologic studies that include a wide range of quantitative data.

All samples were genotyped on the Affymetrix platform. Of those samples 400 were selected for genotyping on the Illumina platform. The selection of the 400 samples was based on the availability of whole genome expression data for these samples. Overall, the study performed genotyping analysis on about 2,600 subjects.

The samples were of three types: clinically diagnosed and neuropathologically confirmed LOAD cases and controls (approximately 2025 samples), neuropathologically characterized samples from a longitudinal epidemiological cohort (approximately 700 samples, some of which qualify as LOAD cases and controls), and antemortem samples from the Banner PET cohort from individuals genetically likely to develop AD (approximately 200 samples). The Rush cohort and PET cohort were used as two endophenotype replication cohorts.

The genotype results from each individual were imputed to increase the genome coverage and also to "clean" the data by re-calling each SNP according to the LD structure and genotype calls of the neighboring SNPs. Extending the SNP set from 1 million to 2.4 million SNPs also allowed for identification of loci with multiple significant SNPs rather than a single significant SNP.

Structure and principle components analysis was used to assess the extent of stratification and admixture in a set of 1,000 unlinked SNPs in each individual. The discovery set includes approximately 2025 LOAD cases (Braak and Braak score V or VI, Cerad B or C, clinical diagnosis of possible or probable Alzheimer's disease) and controls (Braak and Braak score I or II, Cerad 0 or A, no clinical diagnosis of dementia) from several independent cohorts. Power estimates for the discovery cohort are listed below:

TABLE 1

Power to detect effects in the discovery cohort
(alpha = 0.001, two-sided test, D > 0.7)

| Disease Allele Frequency | Allellic Odds Ratio | | |
|---|---|---|---|
| | 1.3 | 1.2 | 1.1 |
| 40% | 100% | 77% | 22% |
| 30% | 99% | 70% | 18% |
| 20% | 97% | 54% | 12% |
| 10% | 77% | 25% | 5% |
| 5% | 37% | 9% | 2% |
| 1% | 9% | 2% | 1% |

Analyses were performed through the use of the following strategies:

A. Single SNP Permutation Analyses

As the number of SNPs increases with denser platforms and imputation, the multiple testing considerations increase, particularly since imputed data sets contain up to 2.4 million SNPs Therefore, maxT permutation analyses was used to control for multiple tests rather than a Bonferroni or Sidak correction, which are likely overly conservative.

B. Quantitative Trait Analyses

Quantitative endophenotype information is available on a portion of the postmortem samples that were genotyped. This information includes data on Braak staging and CERAD plaque estimates. These measures may be analyzed as a quantitative trait against the SNP genotype data to predict SNPs that associate with specific features of LOAD.

C. Set-Association, ReliefF/MDR and Other Compound Analyses

The analyses described above resulted in the identification of several trait-associated SNPs and haplotypes irrespective of potential gene-gene interactions. A pattern of gene interactions was extracted through set-association analyses and other compound genetic analyses in collaboration with the investigators noted above. The level of complexity of the existing interactions was very high in this data set. Therefore, only convergent results from both methods were considered for further evaluation. Set-association evaluates several sets of polymorphic markers throughout the genome and results in a powerful single genome-wide test statistic (See Reference 11). It uses such relevant sources of information as allelic association and Hardy-Weinberg disequilibrium. This information is combined over multiple markers and genes in the genome, quality control is improved by trimming, and permutation tests limit the overall false-positive rate.

Hierarchical cluster analysis was used to allocate significant SNPs and haplotypes to coherent clusters. Among several proximity values and fusion algorithms the weighted average clustering (fusion algorithm) and the simple matching coefficient (proximity value) were selected. The simple matching coefficient is the most suitable proximity value in cases where the values of a binary variable have equal validity. The weighted average clustering (fusion algorithm) is a balanced clustering method, which can be used for every proximity value and is not prone to string formation. Neuman et al. provided evidence for the suitability of cluster analysis in real AD data sets (See Reference 12) and replicated all chromosomal regions formerly identified by using affected-sib-pair methods. While the $\chi^2$- and logistic regression-based analyses aim at identifying novel markers and molecular targets, the set-association and hierarchical cluster analyses will establish the optimal combination of polymorphic markers for diagnosis and, ultimately, prognosis of AD.

Validation of the SNPs listed in Table 2 may be performed using cohorts that have been genotyped, using imputation to test the SNPs. Alternatively, a custom array may be designed. Additionally, fine-mapping or sequencing of the regions around the selected SNPs may be used to identify and/or confirm mutations in coding regions.

TABLE 2

SNPs associated with LOAD

| SNP | Chromosome | BP | Direct P Value |
|---|---|---|---|
| rs429358 | 19 | 50103781 | 4.77E−47 |
| rs4420638 | 19 | 50114786 | 2.05E−45 |
| rs1160985 | 19 | 50095252 | 9.81E−20 |
| rs7412 | 19 | 50103919 | 3.72E−10 |
| rs17042395 | 3 | 16568435 | 6.56E−08 |
| rs16889006 | 5 | 20995156 | 2.55E−07 |
| rs5981380 | 23 | 74791863 | 3.55E−07 |
| rs11066247 | 12 | 111226194 | 4.57E−07 |
| rs4533297 | 16 | 77994546 | 1.82E−06 |
| rs6636980 | 23 | 142420716 | 2.22E−06 |
| rs7895861 | 10 | 54057477 | 2.28E−06 |
| rs6632813 | 23 | 16349702 | 2.50E−06 |
| rs16834130 | 1 | 150731984 | 3.17E−06 |
| rs264256 | 18 | 10921528 | 3.37E−06 |
| rs11217627 | 11 | 119379644 | 4.54E−06 |
| rs13417560 | 2 | 159733535 | 5.11E−06 |
| rs13404031 | 2 | 159754694 | 6.34E−06 |
| rs829465 | 6 | 72488174 | 6.71E−06 |
| rs5955490 | 23 | 139369475 | 6.85E−06 |
| rs1533822 | 16 | 26680632 | 7.12E−06 |
| rs2500144 | 23 | 142948938 | 7.69E−06 |
| rs3112160 | 2 | 38926825 | 7.83E−06 |
| rs11676819 | 2 | 105653813 | 8.91E−06 |
| rs8042680 | 15 | 89322341 | 1.02E−05 |
| rs7908601 | 10 | 92925026 | 1.04E−05 |
| rs40666 | 5 | 9281171 | 1.04E−05 |
| rs9351848 | 6 | 72501745 | 1.09E−05 |
| rs6631389 | 23 | 31703010 | 1.19E−05 |
| rs642612 | 17 | 74033121 | 1.52E−05 |
| rs13033552 | 2 | 123500876 | 1.69E−05 |
| rs35306465 | 4 | 183306697 | 1.78E−05 |
| rs13395944 | 2 | 105655085 | 1.79E−05 |
| rs1204331 | 6 | 72500090 | 1.89E−05 |
| rs9375555 | 6 | 128589687 | 2.12E−05 |
| rs2058810 | 16 | 48516336 | 2.25E−05 |
| rs1634508 | 17 | 31450358 | 2.36E−05 |
| rs2127470 | 15 | 92451058 | 2.39E−05 |
| rs10079121 | 5 | 9281649 | 2.50E−05 |
| rs829467 | 6 | 72489698 | 2.63E−05 |
| rs11097396 | 4 | 77659357 | 2.77E−05 |
| rs10009946 | 4 | 63911889 | 2.79E−05 |
| rs10783282 | 12 | 47433214 | 2.93E−05 |
| rs670139 | 11 | 59728371 | 3.02E−05 |
| rs7064361 | 23 | 57978804 | 3.08E−05 |
| rs16950383 | 16 | 78006279 | 3.08E−05 |
| rs6603530 | 23 | 118572567 | 3.10E−05 |
| rs6709683 | 2 | 105677780 | 3.13E−05 |
| rs4910821 | 11 | 5563215 | 3.19E−05 |
| rs10400909 | 15 | 92450125 | 3.26E−05 |
| rs847386 | 7 | 16941578 | 3.37E−05 |
| rs12186632 | 5 | 114049116 | 3.71E−05 |
| rs1256444 | 15 | 81337307 | 4.05E−05 |
| rs182174 | 21 | 17502225 | 4.22E−05 |
| rs1256428 | 15 | 81318872 | 4.32E−05 |
| rs6094509 | 20 | 35438689 | 4.33E−05 |
| rs5987025 | 23 | 153663006 | 4.44E−05 |
| rs6865969 | 5 | 158435306 | 4.53E−05 |
| rs4547126 | 11 | 5543590 | 4.62E−05 |
| rs4843267 | 16 | 86357971 | 4.74E−05 |
| rs10140673 | 14 | 94211685 | 4.78E−05 |
| rs650943 | 11 | 59763341 | 5.14E−05 |
| rs1130371 | 17 | 31440650 | 5.15E−05 |
| rs3814127 | 9 | 128305563 | 5.15E−05 |
| rs9332441 | 12 | 47357512 | 5.38E−05 |
| rs1954850 | 11 | 101883770 | 5.54E−05 |
| rs11038193 | 11 | 5561289 | 5.54E−05 |
| rs10859338 | 12 | 91472788 | 5.55E−05 |
| rs9784631 | 5 | 29361320 | 5.63E−05 |
| rs6512077 | 19 | 15972223 | 5.85E−05 |
| rs2541286 | 23 | 146541854 | 5.85E−05 |
| rs1943229 | 18 | 56237438 | 6.20E−05 |
| rs2286276 | 7 | 72625290 | 6.27E−05 |
| rs10198042 | 2 | 105634020 | 6.29E−05 |
| rs4286782 | 6 | 55431389 | 6.30E−05 |
| rs7535789 | 1 | 24480006 | 6.31E−05 |
| rs2881599 | 16 | 26677629 | 6.37E−05 |
| rs676309 | 11 | 59758149 | 6.44E−05 |
| rs6552910 | 4 | 186863802 | 6.53E−05 |

TABLE 2-continued

SNPs associated with LOAD

| SNP | Chromosome | BP | Direct P Value |
|---|---|---|---|
| rs17494056 | 2 | 159760977 | 6.70E-05 |
| rs853585 | 10 | 119844853 | 6.85E-05 |
| rs17317101 | 23 | 113232500 | 7.10E-05 |
| rs10504376 | 8 | 65543485 | 7.10E-05 |
| rs10742722 | 11 | 5542948 | 7.21E-05 |
| rs2250392 | 12 | 113458972 | 7.25E-05 |
| rs2881458 | 15 | 84959696 | 7.32E-05 |
| rs16931253 | 8 | 65547912 | 7.35E-05 |
| rs17025061 | 2 | 100943912 | 7.39E-05 |
| rs9309095 | 2 | 43088955 | 7.42E-05 |
| rs4113946 | 12 | 47310287 | 7.61E-05 |
| rs2827909 | 21 | 23442973 | 7.64E-05 |
| rs9904820 | 17 | 43292446 | 7.89E-05 |
| rs4972391 | 2 | 149204738 | 7.94E-05 |
| rs1530914 | 11 | 59785516 | 7.97E-05 |
| rs4794346 | 17 | 47862514 | 7.99E-05 |
| rs11133822 | 5 | 15753541 | 8.20E-05 |
| rs1009987 | 10 | 73337354 | 8.37E-05 |
| rs5962536 | 23 | 104611145 | 8.37E-05 |
| rs1359651 | 20 | 20706593 | 8.42E-05 |
| rs10503040 | 18 | 56230239 | 8.45E-05 |
| rs4090174 | 9 | 131190426 | 8.50E-05 |
| rs17835266 | 11 | 89855586 | 8.52E-05 |
| rs6983226 | 8 | 1944577 | 8.65E-05 |
| rs17865911 | 4 | 118517807 | 8.65E-05 |
| rs1582763 | 11 | 59778524 | 8.67E-05 |
| rs7207413 | 17 | 28806787 | 8.72E-05 |
| rs13013898 | 2 | 123512389 | 8.73E-05 |
| rs1202525 | 1 | 229018521 | 8.79E-05 |
| rs2033494 | 19 | 22392386 | 8.82E-05 |
| rs2956581 | 5 | 36538618 | 9.02E-05 |
| rs40665 | 5 | 9281283 | 9.05E-05 |
| rs9435127 | 1 | 9190296 | 9.06E-05 |
| rs4648858 | 1 | 24479146 | 9.43E-05 |
| rs4648959 | 1 | 24476105 | 9.44E-05 |
| rs1026254 | 11 | 59787033 | 9.63E-05 |
| rs1350089 | 18 | 63151304 | 9.64E-05 |
| rs10402271 | 19 | 50021054 | 9.67E-05 |
| rs10742719 | 11 | 5542828 | 9.74E-05 |
| rs2500153 | 23 | 142964425 | 9.92E-05 |
| rs6817424 | 4 | 81217787 | 9.95E-05 |
| rs466093 | 21 | 30188911 | 0.0001012 |
| rs4746100 | 10 | 73339711 | 0.0001021 |
| rs508915 | 18 | 41686356 | 0.0001028 |
| rs7108663 | 11 | 59784718 | 0.0001033 |
| rs6591559 | 11 | 59782141 | 0.0001037 |
| rs12539316 | 7 | 72615834 | 0.0001039 |
| rs2346709 | 15 | 84959609 | 0.0001057 |
| rs10194269 | 2 | 105660325 | 0.0001057 |
| rs5910606 | 23 | 118555812 | 0.0001071 |
| rs17835397 | 11 | 89857625 | 0.0001081 |
| rs4357331 | 8 | 1925405 | 0.0001092 |
| rs2277365 | 12 | 47362078 | 0.0001094 |
| rs17711743 | 16 | 77996536 | 0.0001095 |
| rs11106228 | 12 | 90561550 | 0.0001099 |
| rs41407844 | 4 | 81219977 | 0.0001108 |
| rs2136342 | 13 | 75617791 | 0.0001109 |
| rs3828191 | 2 | 165058148 | 0.000111 |
| rs16951392 | 17 | 47845191 | 0.000112 |
| rs1479831 | 15 | 92445234 | 0.000113 |
| rs622920 | 13 | 43404671 | 0.0001142 |
| rs4479297 | 17 | 47818557 | 0.0001183 |
| rs11095608 | 23 | 13162923 | 0.0001184 |
| rs5978287 | 23 | 8955187 | 0.0001186 |
| rs9842566 | 3 | 16041190 | 0.0001188 |
| rs953362 | 20 | 20701544 | 0.0001255 |
| rs4289558 | 5 | 15788014 | 0.0001258 |
| rs10512156 | 9 | 86713008 | 0.0001269 |
| rs655231 | 11 | 59770433 | 0.0001279 |
| rs4938931 | 11 | 59783189 | 0.0001281 |
| rs12749061 | 1 | 62102345 | 0.0001282 |
| rs12647148 | 4 | 60424911 | 0.0001294 |
| rs1442063 | 18 | 49377940 | 0.0001317 |
| rs4342343 | 5 | 29350811 | 0.0001317 |
| rs4315367 | 17 | 72030753 | 0.000135 |
| rs4794347 | 17 | 47862591 | 0.0001368 |
| rs1019670 | 11 | 59697175 | 0.0001383 |
| rs11954932 | 5 | 123874867 | 0.0001384 |
| rs4984259 | 15 | 61365054 | 0.0001388 |
| rs2001517 | 18 | 54293292 | 0.0001395 |
| rs6039654 | 20 | 9945251 | 0.00014 |
| rs1409428 | 20 | 20705815 | 0.0001414 |
| rs17145817 | 7 | 72684715 | 0.0001416 |
| rs2278583 | 2 | 42843096 | 0.0001431 |
| rs16931273 | 8 | 65555877 | 0.0001444 |
| rs6654877 | 23 | 8559261 | 0.0001448 |
| rs2603779 | 3 | 16043588 | 0.0001457 |
| rs7051342 | 23 | 107420389 | 0.000146 |
| rs371298 | 23 | 118521354 | 0.0001463 |
| rs12009590 | 23 | 150635183 | 0.000147 |
| rs11698059 | 20 | 20714260 | 0.0001474 |
| rs991110 | 14 | 60877898 | 0.0001478 |
| rs4121392 | 11 | 100148633 | 0.0001481 |
| rs2612600 | 8 | 65510460 | 0.0001496 |
| rs1102617 | 21 | 17521369 | 0.0001502 |
| rs949973 | 5 | 123881433 | 0.0001519 |
| rs11655913 | 17 | 30821778 | 0.0001541 |
| rs3912944 | 23 | 86236218 | 0.0001545 |
| rs953363 | 20 | 20701683 | 0.0001566 |
| rs9555552 | 13 | 108522077 | 0.0001573 |
| rs3120733 | 23 | 154157260 | 0.0001574 |
| rs6137147 | 20 | 20709015 | 0.0001583 |
| rs1277307 | 4 | 57591456 | 0.0001584 |
| rs10077548 | 5 | 123876716 | 0.0001601 |
| rs10900908 | 6 | 1442522 | 0.0001604 |
| rs5981711 | 23 | 74068338 | 0.000162 |
| rs6726524 | 2 | 33612197 | 0.0001637 |
| rs12781952 | 10 | 24741698 | 0.0001647 |
| rs562028 | 11 | 59634426 | 0.000165 |
| rs1026255 | 11 | 59786525 | 0.000166 |
| rs17488034 | 13 | 26314251 | 0.0001674 |
| rs5758223 | 22 | 39819866 | 0.0001674 |
| rs891088 | 19 | 7135762 | 0.0001675 |
| rs1945390 | 11 | 122025463 | 0.0001692 |
| rs831480 | 6 | 37004806 | 0.00017 |
| rs846814 | 9 | 122128253 | 0.0001715 |
| rs12798784 | 11 | 89986271 | 0.0001718 |
| rs7018850 | 9 | 4293517 | 0.000172 |
| rs3813097 | 18 | 72337990 | 0.0001724 |
| rs1377334 | 5 | 114295122 | 0.0001725 |
| rs10869422 | 9 | 70659729 | 0.0001753 |
| rs16852038 | 2 | 215148427 | 0.0001761 |
| rs7161372 | 14 | 91866160 | 0.0001765 |
| rs10426094 | 19 | 7156240 | 0.0001779 |
| rs6473080 | 8 | 79098294 | 0.0001785 |
| rs1123024 | 17 | 28799974 | 0.0001791 |
| rs1618513 | 6 | 6477615 | 0.0001801 |
| rs9434717 | 1 | 9190487 | 0.0001827 |
| rs2827881 | 21 | 23427801 | 0.0001839 |
| rs6914564 | 6 | 135445317 | 0.000185 |
| rs3208856 | 19 | 49988646 | 0.0001881 |
| rs12468287 | 2 | 146070764 | 0.0001902 |
| rs11788891 | 9 | 128246019 | 0.0001911 |
| rs4233036 | 1 | 24475382 | 0.0001918 |
| rs1531347 | 18 | 48432144 | 0.0001944 |
| rs12336107 | 9 | 4300558 | 0.0001944 |
| rs1805957 | 5 | 9287736 | 0.0001964 |
| rs9374351 | 6 | 113064907 | 0.0001984 |
| rs4336923 | 10 | 20409004 | 0.0001993 |
| rs10069190 | 5 | 123879549 | 0.0002017 |
| rs4827479 | 23 | 65574614 | 0.000202 |
| rs10897049 | 11 | 59857157 | 0.0002043 |
| rs1883469 | 20 | 9353485 | 0.0002065 |
| rs1409427 | 20 | 20702959 | 0.0002074 |
| rs589605 | 23 | 144161283 | 0.0002088 |
| rs5966049 | 23 | 145027730 | 0.0002102 |
| rs4510072 | 17 | 28802549 | 0.0002146 |
| rs4643583 | 2 | 56313685 | 0.0002169 |
| rs4744768 | 9 | 77610062 | 0.0002172 |
| rs2232313 | 23 | 129457754 | 0.0002181 |
| rs1596039 | 18 | 46110711 | 0.0002184 |
| rs4964586 | 12 | 106429621 | 0.0002188 |

TABLE 2-continued

SNPs associated with LOAD

| SNP | Chromosome | BP | Direct P Value |
|---|---|---|---|
| rs6542225 | 2 | 115273275 | 0.000219 |
| rs6705923 | 2 | 53037381 | 0.0002209 |
| rs6551575 | 4 | 61216515 | 0.0002211 |
| rs1752653 | 13 | 26220777 | 0.0002228 |
| rs957979 | 17 | 31460821 | 0.0002232 |
| rs4362707 | 3 | 16029235 | 0.0002278 |
| rs2042922 | 5 | 29377058 | 0.0002281 |
| rs41323947 | 1 | 74617191 | 0.0002298 |
| rs820255 | 17 | 71102117 | 0.00023 |
| rs7298828 | 12 | 90558991 | 0.000231 |
| rs2252238 | 12 | 45228174 | 0.0002311 |
| rs5910607 | 23 | 118555830 | 0.0002316 |
| rs7824527 | 8 | 6877608 | 0.0002338 |
| rs2398671 | 5 | 143081401 | 0.000234 |
| rs1805952 | 5 | 9299599 | 0.0002356 |
| rs1719141 | 17 | 31454563 | 0.0002383 |
| rs2503285 | 6 | 104089558 | 0.0002384 |
| rs2728524 | 3 | 2187318 | 0.0002386 |
| rs10819162 | 9 | 128265359 | 0.0002415 |
| rs1553497 | 17 | 28781096 | 0.0002421 |
| rs6683441 | 1 | 217024728 | 0.0002433 |
| rs1879818 | 8 | 141516084 | 0.0002433 |
| rs8015610 | 14 | 94192101 | 0.000244 |
| rs7579138 | 2 | 42838249 | 0.0002446 |
| rs17137349 | 5 | 114369300 | 0.0002447 |
| rs6724143 | 2 | 159693757 | 0.0002454 |
| rs397118 | 23 | 96960172 | 0.0002461 |
| rs12511743 | 4 | 189883970 | 0.0002469 |
| rs1040211 | 15 | 90424674 | 0.0002496 |
| rs2001217 | 15 | 89299250 | 0.0002509 |
| rs12326462 | 18 | 41129825 | 0.0002515 |
| rs17498815 | 12 | 100233988 | 0.0002516 |
| rs10742725 | 11 | 5543121 | 0.000252 |
| rs2224182 | 20 | 11521668 | 0.0002524 |
| rs2834330 | 21 | 34288089 | 0.0002539 |
| rs3745546 | 19 | 7162816 | 0.0002545 |
| rs6535872 | 4 | 153936800 | 0.0002626 |
| rs7249558 | 19 | 58481703 | 0.0002631 |
| rs10514883 | 18 | 54271634 | 0.0002639 |
| rs7243684 | 18 | 46160836 | 0.0002644 |
| rs6577561 | 1 | 9197033 | 0.0002656 |
| rs1256447 | 15 | 81339221 | 0.0002677 |
| rs13382950 | 2 | 227664311 | 0.0002679 |
| rs685859 | 1 | 180040894 | 0.0002701 |
| rs2402961 | 7 | 129192917 | 0.0002709 |
| rs5758267 | 22 | 39949296 | 0.0002711 |
| rs17207648 | 2 | 159673112 | 0.0002718 |
| rs10758597 | 9 | 4291782 | 0.0002727 |
| rs2486027 | 10 | 125294541 | 0.0002739 |
| rs2110706 | 14 | 88925487 | 0.0002757 |
| rs2059129 | 5 | 143076857 | 0.0002757 |
| rs11257695 | 10 | 12385446 | 0.0002796 |
| rs4354335 | 8 | 114475512 | 0.0002799 |
| rs16901211 | 5 | 11080918 | 0.0002809 |
| rs10476994 | 5 | 151059242 | 0.0002826 |
| rs4676320 | 2 | 107130693 | 0.0002832 |
| rs11230180 | 11 | 59718062 | 0.0002837 |
| rs10885864 | 10 | 117895695 | 0.0002851 |
| rs11646101 | 16 | 17231085 | 0.000287 |
| rs4576739 | 10 | 57931414 | 0.0002871 |
| rs9807618 | 18 | 10676131 | 0.0002873 |
| rs1155098 | 8 | 65490948 | 0.0002879 |
| rs2043422 | 8 | 142305519 | 0.0002894 |
| rs6677009 | 1 | 228973577 | 0.0002901 |
| rs2960455 | 7 | 77359883 | 0.0002913 |
| rs7868954 | 9 | 4879208 | 0.0002945 |
| rs10066153 | 5 | 123883295 | 0.0002949 |
| rs2090922 | 8 | 141515495 | 0.0002958 |
| rs34661737 | 7 | 83453919 | 0.0002991 |
| rs5910608 | 23 | 118556154 | 0.0003042 |
| rs610352 | 11 | 59753544 | 0.0003057 |
| rs943218 | 20 | 20715084 | 0.0003073 |
| rs293540 | 20 | 30536829 | 0.0003094 |
| rs2834341 | 21 | 34306691 | 0.0003106 |
| rs7674035 | 4 | 36154894 | 0.0003106 |
| rs10115578 | 9 | 3474373 | 0.0003109 |
| rs13029092 | 2 | 167027829 | 0.0003133 |
| rs9378774 | 6 | 327897 | 0.0003147 |
| rs4283782 | 5 | 123883985 | 0.0003156 |
| rs319858 | 2 | 115247311 | 0.0003182 |
| rs2899683 | 15 | 60725461 | 0.0003186 |
| rs7210605 | 17 | 47861956 | 0.0003189 |
| rs805530 | 20 | 36507613 | 0.0003204 |
| rs718376 | 11 | 59759511 | 0.0003225 |
| rs7069106 | 10 | 92928879 | 0.000324 |
| rs1021632 | 10 | 4642819 | 0.0003244 |
| rs7734932 | 5 | 9281481 | 0.000325 |
| rs2437803 | 15 | 84950790 | 0.0003276 |
| rs717666 | 16 | 26692199 | 0.000328 |
| rs13020250 | 2 | 118248034 | 0.0003282 |
| rs1378169 | 3 | 15985616 | 0.0003291 |
| rs11180553 | 12 | 74196574 | 0.0003302 |
| rs10897003 | 11 | 59594153 | 0.0003305 |
| rs8082463 | 17 | 47820437 | 0.0003316 |
| rs10819174 | 9 | 128307886 | 0.0003325 |
| rs11114028 | 12 | 107620076 | 0.0003327 |
| rs12892914 | 14 | 59849637 | 0.000335 |
| rs2577894 | 8 | 65524163 | 0.0003354 |
| rs999939 | 2 | 85422805 | 0.0003357 |
| rs4953706 | 2 | 43083413 | 0.0003366 |
| rs10430148 | 1 | 24474160 | 0.0003381 |
| rs9424093 | 10 | 10846395 | 0.0003414 |
| rs7577837 | 2 | 146068506 | 0.0003467 |
| rs2289711 | 12 | 27568772 | 0.000347 |
| rs7947761 | 11 | 100129809 | 0.0003473 |
| rs4794225 | 17 | 43312590 | 0.0003487 |
| rs7876084 | 23 | 93516115 | 0.0003492 |
| rs10069118 | 5 | 29375689 | 0.0003498 |
| rs10062543 | 5 | 123876236 | 0.00035 |
| rs7243917 | 18 | 12589042 | 0.0003528 |
| rs11133030 | 4 | 175254410 | 0.000356 |
| rs7872516 | 9 | 109025041 | 0.0003566 |
| rs12555462 | 9 | 106757032 | 0.0003575 |
| rs4961341 | 8 | 142304336 | 0.0003576 |
| rs17522996 | 7 | 47351726 | 0.0003581 |
| rs5951325 | 23 | 100596349 | 0.000359 |
| rs4842993 | 15 | 81504446 | 0.0003601 |
| rs12037865 | 1 | 85467574 | 0.0003602 |
| rs2885856 | 2 | 84049495 | 0.0003614 |
| rs293542 | 20 | 30539357 | 0.0003623 |
| rs7849193 | 9 | 136790645 | 0.0003642 |
| rs12685147 | 9 | 105212719 | 0.0003646 |
| rs1372567 | 6 | 46437363 | 0.0003663 |
| rs6022638 | 20 | 51706144 | 0.0003664 |
| rs17650435 | 11 | 37013796 | 0.0003667 |
| rs10504377 | 8 | 65555633 | 0.0003678 |
| rs880293 | 14 | 94214129 | 0.0003679 |
| rs12037204 | 1 | 115969319 | 0.0003691 |
| rs687582 | 13 | 43405689 | 0.0003718 |
| rs6675497 | 1 | 217024584 | 0.0003726 |
| rs1566106 | 5 | 178278821 | 0.0003727 |
| rs3104996 | 8 | 96632981 | 0.0003729 |
| rs2234246 | 6 | 41351718 | 0.0003731 |
| rs10188267 | 2 | 146069750 | 0.0003746 |
| rs11079804 | 17 | 43375697 | 0.0003769 |
| rs7106518 | 11 | 59596363 | 0.0003771 |
| rs16841583 | 3 | 100853294 | 0.0003773 |
| rs10820403 | 9 | 105045896 | 0.0003776 |
| rs2495988 | 6 | 34065112 | 0.0003786 |
| rs167602 | 11 | 5518171 | 0.0003787 |
| rs1184766 | 3 | 2234929 | 0.0003787 |
| rs7322229 | 13 | 104201563 | 0.0003797 |
| rs4813394 | 20 | 20721090 | 0.0003802 |
| rs16979301 | 23 | 13760577 | 0.0003811 |
| rs3886569 | 11 | 89880510 | 0.0003819 |
| rs8110666 | 19 | 13319662 | 0.000382 |
| rs11073964 | 15 | 89344765 | 0.0003822 |
| rs11889938 | 2 | 105622619 | 0.0003824 |
| rs13037545 | 20 | 10060058 | 0.0003836 |
| rs6716363 | 2 | 205642494 | 0.0003852 |
| rs884771 | 15 | 35290221 | 0.0003878 |
| rs2901098 | 10 | 117884107 | 0.0003889 |

TABLE 2-continued

SNPs associated with LOAD

| SNP | Chromosome | BP | Direct P Value |
|---|---|---|---|
| rs7123220 | 11 | 122013373 | 0.0003889 |
| rs4903240 | 14 | 74105330 | 0.0003911 |
| rs1479560 | 5 | 76504154 | 0.0003938 |
| rs8112746 | 19 | 14891118 | 0.0003941 |
| rs2317481 | 23 | 95073148 | 0.0003943 |
| rs1178520 | 3 | 2235434 | 0.0003953 |
| rs1943783 | 11 | 101863317 | 0.0003992 |
| rs13313001 | 1 | 230386834 | 0.0004018 |
| rs9285657 | 5 | 143077331 | 0.0004029 |
| rs7896662 | 10 | 52547036 | 0.0004034 |
| rs2437801 | 15 | 84951181 | 0.0004034 |
| rs2267346 | 22 | 35337416 | 0.0004063 |
| rs3777530 | 6 | 89966276 | 0.0004065 |
| rs9889183 | 16 | 26691736 | 0.0004093 |
| rs1882569 | 7 | 70371814 | 0.000413 |
| rs12499442 | 4 | 157379583 | 0.0004134 |
| rs5763001 | 22 | 27866549 | 0.0004143 |
| rs12632665 | 3 | 77852817 | 0.000415 |
| rs1124166 | 4 | 120992581 | 0.0004181 |
| rs1372254 | 2 | 141173140 | 0.0004183 |
| rs1719220 | 17 | 31428390 | 0.0004205 |
| rs9652691 | 16 | 80934452 | 0.0004219 |
| rs6082159 | 20 | 20713237 | 0.0004225 |
| rs1124165 | 4 | 120992522 | 0.0004245 |
| rs17091212 | 14 | 94200283 | 0.0004258 |
| rs7499241 | 16 | 77997040 | 0.0004284 |
| rs42495 | 5 | 9284066 | 0.0004288 |
| rs10194172 | 2 | 105660228 | 0.0004296 |
| rs12617390 | 2 | 42838899 | 0.0004302 |
| rs7031164 | 9 | 103645383 | 0.0004318 |
| rs1997608 | 23 | 49326435 | 0.0004327 |
| rs379717 | 5 | 88675886 | 0.0004332 |
| rs17734389 | 2 | 211357028 | 0.0004367 |
| rs6689572 | 1 | 207007565 | 0.0004368 |
| rs4097545 | 9 | 4293313 | 0.0004384 |
| rs1233078 | 5 | 154091321 | 0.0004385 |
| rs10974859 | 9 | 4920487 | 0.0004386 |
| rs8082787 | 18 | 21015369 | 0.00044 |
| rs2110641 | 2 | 10208865 | 0.0004414 |
| rs4903243 | 14 | 74113783 | 0.0004464 |
| rs16964797 | 15 | 35283490 | 0.0004487 |
| rs7250661 | 19 | 18829658 | 0.0004489 |
| rs12909713 | 15 | 84946917 | 0.000449 |
| rs7225545 | 17 | 47849828 | 0.0004504 |
| rs2819190 | 1 | 63992338 | 0.0004529 |
| rs617135 | 11 | 59693333 | 0.0004531 |
| rs12628020 | 22 | 43857825 | 0.0004547 |
| rs12006950 | 23 | 92974264 | 0.0004567 |
| rs9896422 | 17 | 64377091 | 0.000461 |
| rs7164426 | 15 | 84067909 | 0.0004616 |
| rs2356132 | 2 | 8591035 | 0.0004616 |
| rs17091265 | 14 | 94213701 | 0.0004666 |
| rs10897020 | 11 | 59794143 | 0.0004741 |
| rs805531 | 20 | 36508140 | 0.0004753 |
| rs12809801 | 12 | 52922001 | 0.0004765 |
| rs12444393 | 16 | 77998819 | 0.0004777 |
| rs10511964 | 9 | 70577584 | 0.0004781 |
| rs2081547 | 11 | 59746006 | 0.0004791 |
| rs2809591 | 20 | 11711357 | 0.0004803 |
| rs12606449 | 18 | 54303033 | 0.0004813 |
| rs9427206 | 1 | 169203912 | 0.0004827 |
| rs12652190 | 5 | 157125213 | 0.0004846 |
| rs7694032 | 4 | 61235645 | 0.0004876 |
| rs6075709 | 20 | 20709606 | 0.0004877 |
| rs10758596 | 9 | 4291601 | 0.000488 |
| rs4793734 | 17 | 43389104 | 0.0004897 |
| rs17105491 | 10 | 125284396 | 0.0004898 |
| rs17773314 | 5 | 6299957 | 0.0004921 |
| rs10040520 | 5 | 29314106 | 0.0004932 |
| rs6430090 | 2 | 146063929 | 0.0004936 |
| rs4921744 | 8 | 17202683 | 0.0004962 |
| rs17594509 | 4 | 45001935 | 0.0004979 |
| rs293545 | 20 | 30542918 | 0.0004981 |
| rs1108209 | 5 | 7900301 | 0.0004981 |
| rs9405199 | 6 | 3353071 | 0.0005004 |
| rs17253937 | 19 | 7135801 | 0.0005039 |
| rs6621070 | 23 | 100595493 | 0.0005041 |
| rs942950 | 10 | 131705664 | 0.0005052 |
| rs5945088 | 23 | 100986203 | 0.0005054 |
| rs11092309 | 23 | 100624381 | 0.0005058 |
| rs17095429 | 11 | 100144512 | 0.0005076 |
| rs2593529 | 2 | 167057716 | 0.0005076 |
| rs10454797 | 4 | 142235623 | 0.0005086 |
| rs2612589 | 8 | 65526999 | 0.00051 |
| rs2827882 | 21 | 23428112 | 0.0005111 |
| rs6594842 | 5 | 114202964 | 0.0005116 |
| rs9369572 | 6 | 45766359 | 0.0005124 |
| rs6479916 | 10 | 52520061 | 0.0005128 |
| rs492496 | 11 | 51313877 | 0.0005147 |
| rs1566430 | 5 | 165711472 | 0.0005149 |
| rs12910825 | 15 | 89312264 | 0.0005156 |
| rs6557512 | 6 | 157242759 | 0.0005157 |
| rs13381188 | 18 | 49397848 | 0.0005165 |
| rs4147047 | 13 | 41291824 | 0.0005166 |
| rs10819173 | 9 | 128297367 | 0.0005167 |
| rs12318549 | 12 | 129931121 | 0.0005178 |
| rs200545 | 9 | 122137880 | 0.0005181 |
| rs7580100 | 2 | 5197878 | 0.0005185 |
| rs618499 | 11 | 107654049 | 0.0005191 |
| rs2594953 | 8 | 59952764 | 0.0005205 |
| rs7846493 | 8 | 136136037 | 0.0005217 |
| rs1869620 | 4 | 187099677 | 0.0005228 |
| rs7040120 | 9 | 70790991 | 0.0005241 |
| rs667897 | 11 | 59693555 | 0.0005257 |
| rs5756261 | 22 | 35338276 | 0.0005278 |
| rs202869 | 21 | 17485166 | 0.0005281 |
| rs846825 | 9 | 122133808 | 0.0005282 |
| rs11049049 | 12 | 27609898 | 0.0005289 |
| rs11106700 | 12 | 91713188 | 0.0005292 |
| rs2430373 | 14 | 91464063 | 0.0005301 |
| rs32425 | 5 | 50135571 | 0.0005304 |
| rs10777410 | 12 | 91437062 | 0.0005309 |
| rs17383755 | 5 | 114730035 | 0.0005333 |
| rs6749325 | 2 | 10203917 | 0.0005334 |
| rs9324521 | 8 | 136142833 | 0.0005341 |
| rs7737490 | 5 | 112523988 | 0.0005345 |
| rs6451453 | 5 | 39776837 | 0.0005376 |
| rs7722665 | 5 | 157100881 | 0.0005382 |
| rs17465431 | 2 | 123515886 | 0.0005389 |
| rs2879724 | 4 | 157378249 | 0.0005389 |
| rs2635296 | 4 | 118752075 | 0.0005406 |
| rs4956509 | 4 | 142235877 | 0.0005413 |
| rs4975725 | 5 | 2156059 | 0.0005418 |
| rs6729547 | 2 | 159673406 | 0.0005423 |
| rs6555483 | 5 | 7734207 | 0.0005436 |
| rs541965 | 8 | 102703673 | 0.0005454 |
| rs10121466 | 9 | 104797975 | 0.0005461 |
| rs4861498 | 4 | 183306370 | 0.0005472 |
| rs7871777 | 9 | 3519411 | 0.0005504 |
| rs2479505 | 13 | 26228953 | 0.0005521 |
| rs12659288 | 5 | 7755167 | 0.0005525 |
| rs3829304 | 12 | 94588130 | 0.0005536 |
| rs17098400 | 14 | 98745377 | 0.0005537 |
| rs9494139 | 6 | 135456486 | 0.0005539 |
| rs7215182 | 17 | 3665682 | 0.000554 |
| rs7615639 | 3 | 43827569 | 0.0005583 |
| rs7365975 | 1 | 230422758 | 0.0005585 |
| rs1453013 | 5 | 114312438 | 0.0005591 |
| rs3768235 | 1 | 85505962 | 0.0005592 |
| rs11748700 | 5 | 15776346 | 0.0005619 |
| rs673281 | 11 | 107687279 | 0.0005623 |
| rs17332633 | 23 | 23324793 | 0.0005674 |
| rs12107500 | 3 | 100848407 | 0.0005675 |
| rs12658719 | 5 | 30379149 | 0.0005689 |
| rs1467737 | 9 | 124022321 | 0.000569 |
| rs7955859 | 12 | 26230998 | 0.0005704 |
| rs8129151 | 21 | 15611653 | 0.0005713 |
| rs11159907 | 14 | 88928501 | 0.0005741 |
| rs11691971 | 2 | 140611862 | 0.0005744 |
| rs7998410 | 13 | 43411260 | 0.0005787 |
| rs6903671 | 6 | 157257433 | 0.0005789 |
| rs5991907 | 23 | 100602061 | 0.000579 |

TABLE 2-continued

SNPs associated with LOAD

| SNP | Chromosome | BP | Direct P Value |
|---|---|---|---|
| rs846818 | 9 | 122129840 | 0.00058 |
| rs1009940 | 1 | 9200729 | 0.0005853 |
| rs10790519 | 11 | 122040618 | 0.0005854 |
| rs7648664 | 3 | 16007515 | 0.0005855 |
| rs319855 | 2 | 115244200 | 0.0005856 |
| rs2712590 | 12 | 44295788 | 0.000586 |
| rs7625628 | 3 | 16010594 | 0.0005868 |
| rs6828228 | 4 | 83197215 | 0.0005881 |
| rs17039828 | 3 | 14590060 | 0.0005922 |
| rs11752453 | 6 | 1439956 | 0.0005926 |
| rs12375106 | 7 | 150194867 | 0.0005926 |
| rs4514520 | 12 | 123274522 | 0.000593 |
| rs10950254 | 7 | 70375143 | 0.0005935 |
| rs1511556 | 3 | 147865826 | 0.0005946 |
| rs8014761 | 14 | 94192236 | 0.0005947 |
| rs2415025 | 15 | 66716850 | 0.0005949 |
| rs4410671 | 5 | 121262937 | 0.0006046 |
| AFFX-SNP_65923_rs952998 | 1 | 63516479 | 0.0006053 |
| rs4701641 | 5 | 15750062 | 0.0006058 |
| rs1634507 | 17 | 31449687 | 0.0006069 |
| rs10741175 | 10 | 130563773 | 0.0006082 |
| rs6869793 | 5 | 114246813 | 0.0006101 |
| rs7869556 | 9 | 18769533 | 0.0006107 |
| rs4821990 | 22 | 39768656 | 0.0006138 |
| rs293541 | 20 | 30539322 | 0.0006142 |
| rs6603781 | 1 | 1148494 | 0.0006152 |
| rs456298 | 21 | 41758621 | 0.0006156 |
| rs2856044 | 3 | 60583127 | 0.0006158 |
| rs5015994 | 14 | 41903194 | 0.0006159 |
| rs10866514 | 5 | 15742507 | 0.0006167 |
| rs11229192 | 11 | 54875843 | 0.000617 |
| rs4844600 | 1 | 205745930 | 0.0006171 |
| rs980793 | 5 | 39660837 | 0.0006175 |
| rs12238307 | 9 | 3470671 | 0.0006178 |
| rs4695895 | 4 | 175074462 | 0.0006206 |
| rs824631 | 5 | 6498422 | 0.0006217 |
| rs714235 | 20 | 11538160 | 0.0006225 |
| rs9544313 | 13 | 76057418 | 0.0006233 |
| rs11861905 | 16 | 17353902 | 0.0006256 |
| rs11150971 | 18 | 72462172 | 0.0006271 |
| rs1060455 | 19 | 43542270 | 0.000628 |
| rs17135372 | 5 | 112532674 | 0.0006281 |
| rs1352576 | 4 | 118739214 | 0.0006298 |
| rs10878636 | 12 | 66301640 | 0.00063 |
| rs6658884 | 1 | 116004334 | 0.0006305 |
| rs2462645 | 7 | 47352947 | 0.0006306 |
| rs9899379 | 17 | 15024206 | 0.0006327 |
| rs9931815 | 16 | 26696066 | 0.000637 |
| rs10036338 | 5 | 65745783 | 0.0006372 |
| rs4861864 | 4 | 181841004 | 0.0006417 |
| rs17091253 | 14 | 94213193 | 0.0006424 |
| rs9485905 | 6 | 104478463 | 0.0006437 |
| rs11239751 | 10 | 42540291 | 0.0006459 |
| rs11872966 | 18 | 31019308 | 0.0006469 |
| rs10825816 | 10 | 57952174 | 0.0006474 |
| rs11778430 | 8 | 29027477 | 0.0006479 |
| rs2649627 | 1 | 55770993 | 0.0006485 |
| rs11671804 | 19 | 22383056 | 0.000649 |
| rs7821916 | 8 | 136146848 | 0.0006497 |
| rs3960965 | 19 | 58481195 | 0.0006499 |
| rs16931257 | 8 | 65549902 | 0.0006525 |
| rs252977 | 5 | 160663217 | 0.0006532 |
| rs2204608 | 7 | 141278821 | 0.0006533 |
| rs2653322 | 3 | 188771203 | 0.0006545 |
| rs17712565 | 14 | 85123530 | 0.0006549 |
| rs7026025 | 9 | 3469911 | 0.0006571 |
| rs17117632 | 14 | 46315361 | 0.0006583 |
| rs4257715 | 4 | 116830546 | 0.0006587 |
| rs12408105 | 1 | 62084568 | 0.0006591 |
| rs3786954 | 19 | 48964186 | 0.0006625 |
| rs200547 | 9 | 122137243 | 0.0006656 |
| rs12265862 | 10 | 42531656 | 0.0006664 |
| rs275467 | 5 | 6891589 | 0.0006678 |
| rs2455787 | 8 | 140555996 | 0.0006684 |
| rs9654458 | 5 | 7721026 | 0.0006692 |
| rs9964709 | 18 | 3295738 | 0.0006738 |
| rs11694165 | 2 | 160903741 | 0.0006767 |
| rs1416770 | 23 | 145026857 | 0.0006768 |
| rs558514 | 3 | 171892753 | 0.0006799 |
| rs1009947 | 3 | 60583757 | 0.000681 |
| rs1823667 | 8 | 65527548 | 0.0006821 |
| rs738977 | 22 | 35338874 | 0.0006848 |
| rs1883488 | 20 | 9353752 | 0.0006864 |
| rs1604382 | 12 | 74184709 | 0.000687 |
| rs11241620 | 5 | 121252331 | 0.0006872 |
| rs2136343 | 13 | 75617872 | 0.0006874 |
| rs12800777 | 11 | 89866811 | 0.0006882 |
| rs10037238 | 5 | 172642566 | 0.0006942 |
| rs17598123 | 1 | 215095227 | 0.0006943 |
| rs41437548 | 4 | 78918187 | 0.0006959 |
| rs10519170 | 15 | 46473467 | 0.0006972 |
| rs950027 | 15 | 43588327 | 0.0006982 |
| rs7084466 | 10 | 10655422 | 0.0006983 |
| rs3323 | 7 | 47365923 | 0.0007007 |
| rs1798021 | 12 | 43022000 | 0.0007019 |
| rs7199809 | 16 | 64585275 | 0.0007057 |
| rs2812237 | 13 | 50197121 | 0.0007071 |
| rs703374 | 10 | 119343808 | 0.0007074 |
| rs2131361 | 4 | 83199857 | 0.0007092 |
| rs1181913 | 7 | 155701605 | 0.0007104 |
| rs4384677 | 18 | 54305444 | 0.0007112 |
| rs16971511 | 17 | 74040865 | 0.0007128 |
| rs7319447 | 13 | 41449508 | 0.0007131 |
| rs4487976 | 1 | 24818242 | 0.0007135 |
| rs7001207 | 8 | 96523919 | 0.0007135 |
| rs713952 | 22 | 35338433 | 0.0007164 |
| rs7070647 | 10 | 30141225 | 0.0007171 |
| rs252272 | 16 | 29008903 | 0.0007173 |
| rs17095426 | 11 | 100143813 | 0.0007174 |
| rs9394781 | 6 | 41379106 | 0.0007199 |
| rs2025466 | 10 | 10655967 | 0.0007203 |
| rs7423892 | 2 | 161037890 | 0.0007204 |
| rs10773829 | 12 | 129898052 | 0.000721 |
| rs16983551 | 2 | 17426836 | 0.0007211 |
| rs7061770 | 23 | 145017901 | 0.0007252 |
| rs12342299 | 9 | 77832048 | 0.0007262 |
| rs6796090 | 3 | 144793332 | 0.0007269 |
| rs10825817 | 10 | 57953140 | 0.0007273 |
| rs4694116 | 4 | 73163818 | 0.0007273 |
| rs2304935 | 11 | 59858960 | 0.0007282 |
| rs9651363 | 10 | 33169828 | 0.0007288 |
| rs12127313 | 1 | 111655643 | 0.000729 |
| rs848492 | 7 | 77395654 | 0.0007299 |
| rs11016132 | 10 | 129908545 | 0.0007326 |
| rs7495307 | 15 | 64939063 | 0.0007326 |
| rs12648659 | 4 | 137324059 | 0.0007338 |
| rs12495316 | 3 | 156533540 | 0.0007349 |
| rs4393536 | 15 | 84940937 | 0.0007404 |
| rs8057620 | 16 | 68442120 | 0.0007419 |
| rs7316571 | 12 | 27629023 | 0.0007428 |
| rs4237493 | 10 | 117884371 | 0.0007435 |
| rs7666693 | 4 | 45634025 | 0.0007437 |
| rs6770617 | 3 | 16011834 | 0.0007493 |
| rs10515386 | 5 | 107685210 | 0.0007494 |
| rs4701734 | 5 | 6509627 | 0.0007501 |
| rs9395110 | 6 | 45761241 | 0.0007501 |
| rs17255138 | 11 | 89916665 | 0.0007518 |
| rs7071432 | 10 | 117899212 | 0.0007534 |
| rs10477463 | 5 | 110554209 | 0.0007568 |
| rs9812119 | 3 | 14588380 | 0.0007581 |
| rs1256424 | 15 | 81321311 | 0.0007593 |
| rs6546889 | 2 | 74171959 | 0.0007621 |
| rs2694814 | 10 | 117866398 | 0.000763 |
| rs10448254 | 9 | 122147729 | 0.0007648 |
| rs5964670 | 23 | 67550826 | 0.0007654 |
| rs10253781 | 7 | 30880636 | 0.0007662 |
| rs10747215 | 18 | 73359436 | 0.0007669 |
| rs3127080 | 10 | 115497312 | 0.0007703 |
| rs10482042 | 23 | 87395545 | 0.0007717 |
| rs2062368 | 11 | 133299698 | 0.0007724 |
| rs6706570 | 2 | 10203817 | 0.0007733 |

TABLE 2-continued

SNPs associated with LOAD

| SNP | Chromosome | BP | Direct P Value |
|---|---|---|---|
| rs298185 | 8 | 65467757 | 0.0007742 |
| rs6562177 | 13 | 60890016 | 0.0007744 |
| rs12818087 | 12 | 82287661 | 0.0007753 |
| rs3755311 | 2 | 191554448 | 0.0007755 |
| rs17771318 | 10 | 49581363 | 0.000776 |
| rs7825534 | 8 | 96566190 | 0.0007795 |
| rs6800857 | 3 | 186038304 | 0.0007806 |
| rs6458458 | 6 | 45773675 | 0.0007819 |
| rs394457 | 19 | 22022268 | 0.0007824 |
| rs6997082 | 8 | 135903576 | 0.0007863 |
| rs5935673 | 23 | 13793149 | 0.000787 |
| rs2837995 | 21 | 41546340 | 0.0007879 |
| rs9635948 | 18 | 43289577 | 0.0007905 |
| rs7517283 | 1 | 23871196 | 0.0007935 |
| rs1008055 | 8 | 140553899 | 0.0007939 |
| rs1939194 | 11 | 87260772 | 0.0007945 |
| rs35762589 | 2 | 53100421 | 0.0007974 |
| rs13068144 | 3 | 172987423 | 0.0007978 |
| rs1523314 | 3 | 2237692 | 0.0008012 |
| rs10051640 | 5 | 114219275 | 0.000802 |
| rs1366413 | 5 | 7731293 | 0.0008081 |
| rs1149736 | 10 | 79648450 | 0.0008084 |
| rs7031458 | 9 | 84710194 | 0.0008094 |
| rs12595616 | 15 | 89364517 | 0.0008108 |
| rs16830888 | 2 | 135138028 | 0.0008132 |
| rs7679858 | 4 | 34978597 | 0.0008147 |
| rs16863867 | 2 | 223124544 | 0.0008154 |
| rs7018666 | 9 | 89652073 | 0.0008163 |
| rs6861510 | 5 | 134606540 | 0.0008176 |
| rs12446552 | 16 | 11627567 | 0.0008182 |
| rs4562978 | 14 | 42542483 | 0.0008188 |
| rs7152695 | 14 | 101459847 | 0.0008205 |
| rs12601300 | 17 | 21082484 | 0.0008208 |
| rs12922082 | 16 | 25786264 | 0.0008212 |
| rs9872847 | 3 | 83010507 | 0.0008215 |
| rs12191684 | 6 | 163991396 | 0.000822 |
| rs10950253 | 7 | 70375023 | 0.0008225 |
| rs3790971 | 1 | 228973398 | 0.0008231 |
| rs158134 | 5 | 154339352 | 0.000824 |
| rs7018692 | 9 | 70711601 | 0.0008247 |
| rs11858967 | 15 | 84926556 | 0.0008256 |
| rs7878331 | 23 | 102062093 | 0.0008269 |
| rs10787629 | 10 | 117902194 | 0.0008304 |
| rs4306376 | 13 | 106034515 | 0.0008319 |
| rs10814235 | 9 | 3540086 | 0.0008327 |
| rs3781533 | 10 | 117885629 | 0.0008348 |
| rs16918465 | 8 | 110552472 | 0.0008354 |
| rs1079022 | 11 | 45596304 | 0.0008387 |
| rs4307374 | 8 | 136135317 | 0.0008398 |
| rs1039147 | 4 | 91744589 | 0.0008416 |
| rs17431 | 23 | 152709726 | 0.0008462 |
| rs12440774 | 15 | 89283939 | 0.0008482 |
| rs1519812 | 8 | 121114408 | 0.0008511 |
| rs35775016 | 5 | 10141310 | 0.0008528 |
| rs11237698 | 11 | 78435661 | 0.0008536 |
| rs4771531 | 13 | 106032245 | 0.0008541 |
| rs10799801 | 1 | 23877100 | 0.0008542 |
| rs12692593 | 2 | 160905114 | 0.0008545 |
| rs3019879 | 8 | 118086468 | 0.0008571 |
| rs2019707 | 22 | 48055300 | 0.0008572 |
| rs7044778 | 9 | 79466428 | 0.0008579 |
| rs17034079 | 1 | 115972284 | 0.000858 |
| rs12598082 | 16 | 17220789 | 0.0008607 |
| rs10192963 | 2 | 105641096 | 0.0008705 |
| rs10054011 | 5 | 38333961 | 0.0008707 |
| rs2486866 | 10 | 7053222 | 0.0008717 |
| rs2827879 | 21 | 23414584 | 0.0008749 |
| rs10792084 | 11 | 54807466 | 0.0008764 |
| rs7254358 | 19 | 7150341 | 0.0008769 |
| rs4072688 | 10 | 23647331 | 0.0008786 |
| rs802466 | 7 | 86165374 | 0.0008801 |
| rs1395773 | 3 | 97958596 | 0.0008807 |
| rs12632797 | 3 | 193577438 | 0.0008818 |
| rs11741205 | 5 | 49941566 | 0.0008827 |
| rs10515026 | 17 | 48205748 | 0.0008832 |
| rs236573 | 17 | 65736802 | 0.0008838 |
| rs11914999 | 3 | 110134703 | 0.0008841 |
| rs6498220 | 16 | 11548039 | 0.0008847 |
| rs40353 | 19 | 44571503 | 0.0008851 |
| rs1959185 | 14 | 83182702 | 0.0008893 |
| rs2273235 | 5 | 149887726 | 0.00089 |
| rs9291171 | 4 | 73200490 | 0.0008935 |
| rs17410182 | 4 | 79101107 | 0.000895 |
| rs7595401 | 2 | 74117716 | 0.0008988 |
| rs5907046 | 23 | 139533442 | 0.0008993 |
| rs2166500 | 2 | 43022776 | 0.0009024 |
| rs11647759 | 16 | 26694452 | 0.0009041 |
| rs7297136 | 12 | 53264138 | 0.0009063 |
| rs7532358 | 1 | 61893169 | 0.0009083 |
| rs5992600 | 22 | 15831710 | 0.0009095 |
| rs10792267 | 11 | 59858294 | 0.0009125 |
| rs559664 | 11 | 69041441 | 0.0009132 |
| rs1284059 | 18 | 13766822 | 0.0009134 |
| rs10915495 | 1 | 3929593 | 0.0009161 |
| rs1332249 | 9 | 122142868 | 0.0009173 |
| rs9914336 | 17 | 67814383 | 0.0009188 |
| rs11738432 | 5 | 157122196 | 0.0009193 |
| rs1362729 | 18 | 23396044 | 0.0009201 |
| rs16854702 | 2 | 168657480 | 0.0009205 |
| rs16943700 | 17 | 55055363 | 0.0009216 |
| rs7076076 | 10 | 73349651 | 0.0009224 |
| rs17237607 | 3 | 126170122 | 0.0009228 |
| rs16900667 | 8 | 126596016 | 0.0009246 |
| rs13302146 | 9 | 105053258 | 0.0009266 |
| rs4652931 | 1 | 37098670 | 0.0009279 |
| rs9706460 | 12 | 45148787 | 0.0009286 |
| rs10231253 | 7 | 157676114 | 0.0009294 |
| rs1109916 | 1 | 230384567 | 0.0009295 |
| rs9472557 | 6 | 45784786 | 0.0009311 |
| rs2139615 | 2 | 176986713 | 0.0009326 |
| rs4506675 | 11 | 59858169 | 0.0009329 |
| rs1685513 | 3 | 2238690 | 0.0009358 |
| rs7753479 | 6 | 153064844 | 0.0009359 |
| rs6569979 | 6 | 135278851 | 0.0009367 |
| rs2139109 | 2 | 105458724 | 0.0009378 |
| rs6800578 | 3 | 144995427 | 0.0009382 |
| rs17797399 | 16 | 77899455 | 0.0009384 |
| rs1547329 | 13 | 21934103 | 0.0009444 |
| rs2017823 | 18 | 2373523 | 0.000945 |
| rs1460191 | 18 | 48435190 | 0.0009455 |
| rs627178 | 1 | 40900563 | 0.0009455 |
| rs17048072 | 4 | 116893093 | 0.0009467 |
| rs12395571 | 23 | 87125037 | 0.0009469 |
| rs17600575 | 4 | 163548786 | 0.0009477 |
| rs2034085 | 15 | 89307456 | 0.0009494 |
| rs16852953 | 1 | 202371798 | 0.0009499 |
| rs1772988 | 6 | 2457119 | 0.0009511 |
| rs41390747 | 4 | 116842242 | 0.0009512 |
| rs10733121 | 1 | 236705735 | 0.000953 |
| rs9267135 | 6 | 31545596 | 0.0009539 |
| rs1881441 | 17 | 55053802 | 0.000954 |
| rs2834344 | 21 | 34312918 | 0.0009575 |
| rs11133602 | 5 | 10157640 | 0.000958 |
| rs16959238 | 17 | 61849811 | 0.0009593 |
| rs7290458 | 22 | 39806283 | 0.0009613 |
| rs9909601 | 17 | 30841535 | 0.0009617 |
| rs4241009 | 1 | 141510591 | 0.0009627 |
| rs2242945 | 21 | 39389293 | 0.0009629 |
| rs10974449 | 9 | 4301035 | 0.0009659 |
| rs4898872 | 14 | 55287379 | 0.0009665 |
| rs11629688 | 15 | 52771380 | 0.0009697 |
| rs9652690 | 16 | 80934409 | 0.0009708 |
| rs13053558 | 22 | 18061827 | 0.000971 |
| rs16863859 | 1 | 169187683 | 0.0009721 |
| rs552409 | 11 | 56326588 | 0.0009724 |
| rs12686342 | 9 | 105216557 | 0.0009726 |
| rs16914456 | 12 | 18712672 | 0.0009736 |
| rs3913840 | 18 | 4436168 | 0.0009797 |
| rs10988348 | 9 | 131192369 | 0.0009801 |
| rs4382847 | 10 | 52236981 | 0.0009805 |
| rs12316258 | 12 | 26230484 | 0.0009806 |
| rs624761 | 1 | 18917464 | 0.0009824 |

TABLE 2-continued

SNPs associated with LOAD

| SNP | Chromosome | BP | Direct P Value |
|---|---|---|---|
| rs10945913 | 6 | 163986705 | 0.0009827 |
| rs914593 | 9 | 122210031 | 0.0009828 |
| rs12196957 | 6 | 2474780 | 0.0009856 |
| rs9520114 | 13 | 106045240 | 0.0009863 |
| rs1993471 | 15 | 58827317 | 0.0009863 |
| rs17643262 | 19 | 50323656 | 0.0009874 |
| rs1537989 | 9 | 128281645 | 0.0009874 |
| rs3822459 | 5 | 39427301 | 0.0009889 |
| rs11584403 | 1 | 153011655 | 0.0009954 |
| rs7148564 | 14 | 22893753 | 0.000996 |
| rs41447448 | 1 | 115992668 | 0.0009995 |
| rs2827911 | 21 | 23443694 | 0.001 |
| rs2288522 | 19 | 60400287 | 0.001002 |
| rs7120207 | 11 | 98486432 | 0.001004 |
| rs2152649 | 9 | 70726326 | 0.001004 |
| rs10267678 | 7 | 30894507 | 0.001005 |
| rs11170973 | 12 | 53251464 | 0.001006 |
| rs9776031 | 9 | 105068478 | 0.001007 |
| rs11218016 | 11 | 120199964 | 0.001009 |
| rs12969851 | 18 | 58105791 | 0.001009 |
| rs16879693 | 8 | 110596605 | 0.001009 |
| rs227103 | 1 | 69914136 | 0.00101 |
| rs12313149 | 12 | 100108354 | 0.001013 |
| rs1918676 | 18 | 10751757 | 0.001013 |
| rs1471994 | 3 | 76197670 | 0.001014 |
| rs1805960 | 5 | 9268331 | 0.001014 |
| rs1417032 | 10 | 7052468 | 0.001015 |
| rs958935 | 3 | 113753102 | 0.001015 |
| rs4862558 | 4 | 186829632 | 0.001016 |
| rs1111218 | 16 | 64602993 | 0.001017 |
| rs614013 | 11 | 123697134 | 0.001018 |
| rs3118077 | 13 | 50200311 | 0.001018 |
| rs12084240 | 1 | 23853039 | 0.001022 |
| rs4743641 | 9 | 105107354 | 0.001024 |
| rs11710973 | 3 | 55192552 | 0.001025 |
| rs252950 | 5 | 160647177 | 0.001025 |
| rs41381844 | 5 | 110683591 | 0.001025 |
| rs4537793 | 11 | 117558366 | 0.00103 |
| rs7220146 | 17 | 55081473 | 0.001031 |
| rs4369216 | 1 | 229264955 | 0.001033 |
| rs7773435 | 6 | 1282034 | 0.001037 |
| rs853389 | 6 | 14298744 | 0.001038 |
| rs5956359 | 23 | 120693513 | 0.001039 |
| rs10892873 | 11 | 122040543 | 0.00104 |
| rs2181987 | 14 | 60887286 | 0.001041 |
| rs7856017 | 9 | 29942326 | 0.001041 |
| rs802441 | 7 | 86125039 | 0.001042 |
| rs7197825 | 16 | 64590533 | 0.001043 |
| rs17087898 | 9 | 86743031 | 0.001044 |
| rs10515029 | 17 | 48243948 | 0.001045 |
| rs9812150 | 3 | 134104645 | 0.001046 |
| rs2213369 | 23 | 100906897 | 0.001047 |
| rs7212136 | 17 | 22593769 | 0.00105 |
| rs1719210 | 17 | 31460104 | 0.001051 |
| rs10773890 | 12 | 130421426 | 0.001053 |
| rs971354 | 4 | 46797872 | 0.00106 |
| rs1081900 | 3 | 120034411 | 0.001062 |
| rs217034 | 7 | 140652473 | 0.001062 |
| rs16995332 | 20 | 1500457 | 0.001063 |
| rs4978968 | 9 | 112734176 | 0.001063 |
| rs9999758 | 4 | 135959118 | 0.001066 |
| rs9898218 | 17 | 43461633 | 0.001067 |
| rs9651104 | 1 | 212070341 | 0.001067 |
| rs2031183 | 13 | 112905688 | 0.001068 |
| rs1966374 | 4 | 15523132 | 0.001068 |
| rs9504837 | 6 | 6473946 | 0.001068 |
| rs1023964 | 2 | 146076321 | 0.001071 |
| rs2398485 | 12 | 128843148 | 0.001072 |
| rs17654608 | 4 | 53878489 | 0.001072 |
| rs783376 | 6 | 117548067 | 0.001072 |
| rs11143837 | 9 | 76014104 | 0.001072 |
| rs10848219 | 12 | 129898081 | 0.001073 |
| rs2203432 | 2 | 98801190 | 0.001073 |
| rs17133758 | 11 | 98916596 | 0.001074 |
| rs10031360 | 4 | 126958283 | 0.001075 |
| rs2900285 | 9 | 132075459 | 0.001075 |
| rs2040507 | 16 | 71581088 | 0.001077 |
| rs1939184 | 11 | 87266534 | 0.00108 |
| rs12513052 | 4 | 181646595 | 0.001081 |
| rs2057915 | 7 | 140653479 | 0.001081 |
| rs12294703 | 11 | 27190421 | 0.001084 |
| rs2447265 | 15 | 84954786 | 0.001084 |
| rs865671 | 6 | 14735136 | 0.001084 |
| rs1346440 | 5 | 134600906 | 0.001085 |
| rs16879230 | 7 | 33765580 | 0.001086 |
| rs4421130 | 5 | 36617671 | 0.001087 |
| rs7606424 | 2 | 176986683 | 0.001088 |
| rs17236661 | 4 | 77415500 | 0.00109 |
| rs4829946 | 23 | 137800274 | 0.001092 |
| AFFX-SNP_9234256_rs636147 | 11 | 59713668 | 0.001095 |
| rs11947861 | 4 | 189873341 | 0.001096 |
| rs7726558 | 5 | 118940497 | 0.001096 |
| rs890731 | 5 | 134602305 | 0.001098 |
| rs7699718 | 4 | 79098485 | 0.001099 |
| rs9329143 | 5 | 177698849 | 0.001099 |
| rs12225299 | 11 | 59841041 | 0.001103 |
| rs4864737 | 4 | 53797470 | 0.001103 |
| rs10110144 | 8 | 121074896 | 0.001103 |
| rs8070132 | 17 | 55144988 | 0.001104 |
| rs4961257 | 8 | 142301886 | 0.001105 |
| rs2624938 | 6 | 2474303 | 0.001106 |
| rs4955753 | 3 | 171962804 | 0.001107 |
| rs4555926 | 6 | 153061594 | 0.001107 |
| rs4978970 | 9 | 112737852 | 0.001112 |
| rs7190355 | 16 | 64601406 | 0.001114 |
| rs298069 | 5 | 59013969 | 0.001114 |
| rs759112 | 23 | 36748565 | 0.001116 |
| rs321325 | 6 | 45785076 | 0.001119 |
| rs7086393 | 10 | 57920476 | 0.001122 |
| rs1478281 | 8 | 4477685 | 0.001123 |
| rs7084673 | 10 | 94157067 | 0.001124 |
| rs8006542 | 14 | 88733952 | 0.001131 |
| rs7603548 | 2 | 43018651 | 0.001132 |
| rs4875330 | 8 | 4164349 | 0.001132 |
| rs1002261 | 9 | 86756127 | 0.001136 |
| rs16864008 | 2 | 223266030 | 0.001138 |
| rs11133248 | 4 | 53752859 | 0.001138 |
| rs7082405 | 10 | 608841 | 0.001142 |
| rs17599877 | 5 | 126216415 | 0.001142 |
| rs2954892 | 8 | 114552699 | 0.001143 |
| rs28515959 | 23 | 135648246 | 0.001145 |
| rs4699882 | 5 | 65944332 | 0.001148 |
| rs17056952 | 9 | 73341612 | 0.001148 |
| rs10198317 | 2 | 53807627 | 0.001149 |
| rs2833325 | 21 | 31470453 | 0.00115 |
| rs3104993 | 8 | 96641338 | 0.00115 |
| rs1393360 | 3 | 79931615 | 0.001151 |
| rs12829992 | 12 | 96604014 | 0.001155 |
| rs7294982 | 12 | 44290428 | 0.001158 |
| rs7517009 | 1 | 204082615 | 0.001163 |
| rs7702491 | 5 | 8050545 | 0.001163 |
| rs2160491 | 16 | 47603070 | 0.001164 |
| rs6577853 | 8 | 135890845 | 0.001164 |
| rs6123167 | 20 | 35990953 | 0.001168 |
| rs4272222 | 6 | 53857633 | 0.001168 |
| rs2382492 | 9 | 14621836 | 0.001169 |
| rs7203844 | 16 | 47606386 | 0.00117 |
| rs9390645 | 6 | 149317560 | 0.00117 |
| rs1540125 | 11 | 78147371 | 0.001174 |
| rs17602572 | 11 | 59704950 | 0.001175 |
| rs11266413 | 23 | 78430327 | 0.001177 |
| rs4639843 | 10 | 12389096 | 0.001178 |
| rs2544081 | 12 | 44301754 | 0.001178 |
| rs12123186 | 1 | 236969721 | 0.001178 |
| rs2997967 | 1 | 235667890 | 0.001179 |
| rs641118 | 1 | 180054971 | 0.001181 |
| rs4898337 | 23 | 101288908 | 0.001182 |
| rs9780606 | 23 | 149072768 | 0.001182 |
| rs6966132 | 7 | 24866686 | 0.001182 |
| rs4316805 | 17 | 29063736 | 0.001183 |
| rs9376083 | 6 | 135393413 | 0.001185 |

TABLE 2-continued

SNPs associated with LOAD

| SNP | Chromosome | BP | Direct P Value |
|---|---|---|---|
| rs17016207 | 4 | 143624532 | 0.001186 |
| rs35393495 | 8 | 13091178 | 0.001186 |
| rs7196364 | 16 | 7411668 | 0.001187 |
| rs16857593 | 2 | 11593040 | 0.001187 |
| rs2880301 | 13 | 18998534 | 9.27E-11 |
| rs7412 | 19 | 50103919 | 3.72E-10 |
| rs12741415 | 1 | 200741397 | 2.49E-09 |
| rs1778596 | 1 | 143702635 | 4.46E-09 |
| rs12723357 | 1 | 241185135 | 5.61E-09 |
| rs17042395 | 3 | 16568435 | 6.56E-08 |
| rs10199416 | 2 | 143462845 | 7.69E-08 |
| rs429358 | 19 | 50103781 | 4.77E-47 |
| rs2898441 | 21 | 41528394 | 0.04743 |
| rs4420638 | 19 | 50114786 | 2.05E-45 |

In all SNPs shown in Table 2, the association is in reference to the minor allele in the Caucasian population.

Example 2

Identification of an Allele Associated with Reduced Risk of LOAD

Numerous SNPs on each chromosome of the human genome have been found to be associated with LOAD. The rs17042395 SNP on chromosome 3 was found to be significantly associated with altered Alzheimer's disease (AD) risk in the APOE E3/E3 group. These individuals are homozygous for the neutral form of the APOE risk allele. APOE is the strongest most replicated AD risk locus. Thus as determined during development of the present invention, when risk at the APOE locus is controlled for, a significant (surviving genome-wide hypothesis correction) association with altered AD risk at this SNP is observed. Remarkably, this SNP survives multiple hypothesis correction.
P-value (logistic regression): 2.72E-08
Odds Ratio=0.4045 (for the A-allele)
Location: Chr. 3, BP 16568435
SNP ID: rs17042395
The sequence surrounding rs17042395 SNP is set forth as SEQ ID NO:1 with R=A or G:

```
The sequence surrounding rs17042395 SNP is set
forth as SEQ ID NO: 1 with R = A or G:
AAAGAAAGGG GAAAGAAAAG GTATATTTGA AATGGAGACA

TAGCCCAAGG CTCTTAAACT CAGGGTTATG TCAGTCATGA

TGTAATAAAA TCATGAGGCC CTACATATAT TGTTTTTCTC

CTTTTGGTAT AAGCTTGGGT TTCAGAGCCA TGTTTTTCGA

CGCCAGTAAA ACTTCCAGCA CTAGCATGGA AATGAACTGC

AGTCGATGGC TGCCCTCAAG GTTGGAGAGG GGATAGGAAA

CTGGGGCTGC

R
TTGAACTGGA CAACACTTGT CTGGTCTCAG GTGGATGACT

GGTGTCAGCC CAGAATGGCC AGGAGGTGTG GCAAGATTTT

CCTGTTTGCC TAAAGAAAGT AACCACTTGG GATCTCCTGC

TTGTAAATGT TGGCCCAAGT TTTTGAACTC TACAGGGGCT

AAAGAAATCA TCCCCGAGGA CTGAGTTCAG CTTGTGGGTC

TCCAGCTTGC GCTCTCTGCT GTTCATTGCT ATAGTCTTGC

AAGAAGGTGG.

The "A" allele of rs17042395 (SEQ ID NO: 2):
GAGAGGGGATAGGAAACTGGGGCTGCATTGAACTGGACAACACTTGTCT

GGT.

The "G" allele of rs17042395 (SEQ ID NO: 3):
GAGAGGGGATAGGAAACTGGGGCTGCGTTGAACTGGACAACACTTGTCT

GGT.
```

Accordingly, this SNP is useful for diagnostic applications in non-carriers of the APOE risk allele (E4 allele). The rs17042395 SNP does not lie directly within any known gene in the human genome. Neighboring genes include RFTN1, DAZL, and an uncharacterized transcript, BC034913. Thus, these three genes represent novel targets for AD, especially for individuals that do not carry the APOE E4 risk allele.

REFERENCES

The references cited herein are expressly incorporated by reference to the extent allowed, as well as all of the following materials.
1. Ritchie K and Kildea D, *Lancet* 346, 931-94 (1995).
2. Gatz M et al, *J Gerontol A Biol Sci Med Sci* 52, M117-M125 (1997).
3. Ashford J W and Mortimer J A, *J Alzheimers Dis* 4, 169-177 (2002).
4. Tanzi R E, and Bertram L. *Neuron* 32, 181-184 (2001).
5. Zubenko G S et al, *Genomics* 50, 121-128 (1998).
6. Kehoe P et al, *Hum Mol Genet* 8, 237-245 (1999).
7. Myers A et al, *Am J Med Genet* 114, 235-244 (2002).
8. Risch N and Merikangas K, *Science* 273, 1516-1517 (1996).
9. Coon K D et al, *J Clin Psychiatry* 68, 613-618 (2007).
10. Reiman E M et al, *Neuron.* 54, 713-720 (2007).
11. Hoh J et al, *Genome Res* 11, 2115-2119 (2001).
12. Neuman R J et al, *Genet Epidemiol* 19, S57-63 (2000).

We claim:

1. A method of classifying a subject to a late onset Alzheimer's disease (LOAD) risk group, comprising:
    receiving a sample from the subject;
    detecting a first marker selected from the group consisting of rs10009946, rs1002261, rs10031360, rs10036338, rs10037238, rs10040520, rs10051640, rs10054011, rs10062543, rs10066153, rs10069118, rs10069190, rs10077548, rs10079121, rs1008055, rs1009940, rs1009947, rs1009987, rs10110144, rs10115578, rs10121466, rs10140673, rs10188267, rs10192963, rs10194172, rs10194269, rs1019670, rs10198042, rs10198317, rs10199416, rs1021632, rs10231253, rs1023964, rs10253781, rs1026254, rs1026255, rs10267678, rs1039147, rs10400909, rs1040211, rs10402271, rs10426094, rs10430148, rs10448254, rs10454797, rs10476994, rs10477463, rs10482042, rs10503040, rs10504376, rs10504377, rs10511964, rs10512156, rs10514883, rs10515026, rs10515029, rs10515386, rs10519170, rs1060455, rs10733121, rs10741175, rs10742719, rs10742722, rs10742725, rs10747215, rs10758596, rs10758597, rs10773829, rs10773890, rs10777410, rs10783282, rs10787629, rs1079022, rs10790519, rs10792084, rs10792267, rs10799801, rs10814235, rs1081900, rs10819162, rs10819173, rs10819174, rs10820403, rs10825816, rs10825817, rs10848219, rs10859338, rs10866514, rs10869422, rs10878636, rs10885864, rs10892873, rs10897003, rs10897020, rs10897049, rs10900908, rs10915495, rs10945913, rs10950253, rs10950254, rs10974449, rs10974859, rs10988348, rs11016132, rs1102617, rs11038193, rs11049049, rs11066247, rs11073964, rs11079804, rs1108209, rs11092309, rs11095608, rs11097396, rs1109916, rs11106228, rs11106700, rs1111218, rs11114028, rs11133030, rs11133248, rs11133602, rs11133822, rs11143837, rs11150971, rs11159907, rs11170973, rs11180553, rs11217627, rs11218016, rs11229192, rs11230180, rs1123024, rs11237698, rs11239751, rs11241620, rs1124165, rs1124166, rs11257695, rs11266413, rs1130371, rs1149736, rs1155098, rs11584403, rs1160985, rs11629688, rs11646101, rs11647759, rs11655913, rs11671804, rs11676819, rs11691971, rs11694165, rs11698059, rs11710973, rs11738432, rs11741205, rs11748700, rs11752453, rs11778430, rs1178520, rs11788891, rs1181913, rs1184766, rs11858967, rs11861905, rs11872966, rs11889938, rs11914999, rs11947861, rs11954932, rs12006950, rs12009590, rs1202525, rs12037204, rs12037869, rs1204331, rs12084240, rs12107500, rs12123186, rs12127313, rs12186632, rs12191684, rs12196957, rs12225299, rs12238307, rs12265862, rs12294703, rs12313149, rs12316258, rs12318549, rs12326462, rs1233078, rs12336107, rs12342299, rs12375106, rs12395571, rs12408105, rs12440774, rs12444393, rs12446552, rs12468287, rs12495316, rs12499442, rs12511743, rs12513052, rs12539316, rs12555462, rs1256424, rs1256428, rs1256444, rs1256447, rs12595616, rs12598082, rs12601300, rs12606449, rs12617390, rs12628020, rs12632665, rs12632797, rs12647148, rs12648659, rs12652190, rs12658719, rs12659288, rs12685147, rs12686342, rs12692593, rs12723357, rs12741415, rs12749061, rs1277307, rs12781952, rs12798784, rs12800777, rs12809801, rs12818087, rs12829992, rs1284059, rs12892914, rs12909713, rs12910825, rs12922082, rs12969851, rs13013898, rs13020250, rs13029092, rs13033552, rs13037545, rs13053558, rs13068144, rs13302146, rs13313001, rs1332249, rs13381188, rs13382950, rs13395944, rs13404031, rs13417560, rs1346440, rs1350089, rs1352576, rs1359651, rs1362729, rs1366413, rs1372254, rs1372567, rs1377334, rs1378169, rs1393360, rs1395773, rs1409427, rs1409428, rs1416770, rs1417032, rs1442063, rs1453013, rs1460191, rs1467737, rs1471994, rs1478281, rs1479560, rs1479831, rs1511556, rs1519812, rs1523314, rs1530914, rs1531347, rs1533822, rs1537989, rs1540125, rs1547329, rs1553497, rs1566106, rs1566430, rs158134, rs1582763, rs1596039, rs1604382, rs1618513, rs1634507, rs1634508, rs167602, rs16830888, rs16834130, rs16841583, rs16852038, rs16852953, rs16854702, rs1685513, rs16857593, rs16863859, rs16863867, rs16864008, rs16879230, rs16879693, rs16889006, rs16900667, rs16901211, rs16914456, rs16918465, rs16931253, rs16931257, rs16931273, rs16943700, rs16950383, rs16951392, rs16959238, rs16964797, rs16971511, rs16979301, rs16983551, rs16995332, rs17016207, rs17025061, rs17034079, rs17039828, rs17042395, rs17048072, rs17056952, rs17087898, rs17091212, rs17091253, rs17091265, rs17095426, rs17095429, rs17098400, rs17105491, rs17117632, rs17133758, rs17135372, rs17137349, rs17145817, rs1719141, rs1719210, rs1719220, rs17207648, rs17236661, rs17237607, rs17253937, rs17255138, rs17317101, rs17332633, rs17383755, rs17410182, rs17431, rs17465431, rs17488034, rs17494056, rs17498815, rs17522996, rs1752653, rs17594509, rs17598123, rs17599877, rs17600575, rs17602572, rs17643262, rs17650435, rs17654608, rs17711743, rs17712565, rs1772988, rs17734389, rs17771318, rs17773314, rs1778596, rs17797399, rs17835266, rs17835397, rs17865911, rs1798021, rs1805952, rs1805957, rs1805960, rs182174, rs1823667, rs1869620, rs1879818, rs1881441, rs1882569, rs1883487, rs1883488, rs1918676, rs1939184, rs1939194, rs1943229, rs1943783, rs1945390, rs1954850, rs1959185, rs1966374, rs1993471, rs1997608, rs2001217, rs2001517, rs200545, rs200547, rs2017823, rs2019707, rs2025466, rs202869, rs2031183, rs2033494, rs2034085, rs2040507, rs2042922, rs2043422, rs2057915, rs2058810, rs2059129, rs2062368, rs2081547, rs2090922, rs2110641, rs2110706, rs2127470, rs2131361, rs2136342, rs2136343, rs2139109, rs2139615, rs2152649, rs2160491, rs2166500, rs217034, rs2181987, rs2203432, rs2204608, rs2213369, rs2224182, rs2232313, rs2234246, rs2242945, rs2250392, rs2252238, rs2267346, rs227103, rs2273235, rs2277365, rs2278583, rs2286276, rs2288522, rs2289711, rs2304935, rs2317481, rs2346709, rs2356132, rs236573, rs2382492, rs2398485, rs2398671, rs2402961, rs2415025, rs2430373, rs2437801, rs2437803, rs2447265, rs2455787, rs2462645, rs2479505, rs2486027, rs2486866, rs2495988, rs2500144, rs2500153, rs2503285, rs252272, rs252950, rs252977, rs2541286, rs2544081, rs2577894, rs2593529, rs2594953, rs2603779, rs2612589, rs2612600, rs2624938, rs2635296, rs264256, rs2649627, rs2653322, rs2694814, rs2712590, rs2728524, rs275467, rs2809591, rs2812237, rs2819190, rs2827879, rs2827881, rs2827882, rs2827909, rs2827911, rs2833325, rs2834330, rs2834341, rs2834344, rs2837995, rs28515995, rs2856044, rs2879724, rs2880301, rs2881458, rs2881599, rs2885856, rs2898441, rs2899683, rs2900285, rs2901098, rs293540, rs293541, rs293542, rs293545, rs2954892, rs2956581, rs2960455, rs298069, rs298185, rs2997967, rs3019879, rs3104993, rs3104996, rs3112160, rs3118077, rs3120733, rs3127080, rs319855, rs319858, rs3208856, rs321325, rs32425, rs3323, rs34661737, rs35306465, rs35393495, rs35762589, rs35775016, rs371298, rs3745546, rs3755311, rs3768235, rs3777530, rs3781533, rs3786954, rs3790971, rs379717, rs3813097, rs3814127, rs3822459, rs3828191, rs3829304, rs3886569, rs3912944, rs3913840, rs394457, rs3960965, rs397118, rs40353, rs40665, rs40666, rs4072688, rs4090174, rs4097545, rs4113946, rs4121392, rs41323947, rs41381844, rs41390747, rs41407844, rs41437548, rs41447448, rs4147047, rs4233036, rs4237493, rs4241009, rs42495, rs4257715, rs4272222, rs4283782, rs4286782, rs4289558, rs4306376, rs4307374, rs4315367, rs4316805, rs4336923, rs4342343, rs4354335, rs4357331, rs4362707, rs4369216, rs4382847, rs4384677, rs4393536, rs4410671, rs4420638, rs4421130, rs4479297, rs4487976, rs4506675, rs4510072, rs4514520, rs4533297, rs4537793, rs4547126, rs4555926, rs4562978, rs456298, rs4576739, rs4639843, rs4643583, rs4648858, rs4648959, rs4652931, rs466093, rs4676320, rs4694116, rs4695895, rs4699882, rs4701641, rs4701734, rs4743641, rs4744768, rs4746100, rs4771531, rs4793734, rs4794225, rs4794346, rs4794347, rs4813394, rs4821990, rs4827479, rs4829946, rs4842993, rs4843267, rs4844600, rs4861498, rs4861864, rs4862558, rs4864737, rs4875330, rs4898337, rs4898872, rs4903240, rs4903243, rs4910821, rs4921744, rs492496, rs4938931, rs4953706, rs4955753, rs4956509, rs4961257, rs4961341, rs4964586, rs4972391, rs4975725, rs4978968, rs4978970, rs4984259, rs5015994, rs508915, rs541965, rs552409, rs558514, rs559664, rs562028, rs5756261, rs5758223, rs5758267, rs5763001, rs589605, rs5907046, rs5910606, rs5910607, rs5910608, rs5935673, rs5945088, rs5951325, rs5955490, rs5956359, rs5962536, rs5964670, rs5966049, rs5978287, rs5981380, rs5981711, rs5987025, rs5991907, rs5992600, rs6022638, rs6039654, rs6075709, rs6082159, rs6094509, rs610352, rs6123167, rs6137147, rs614013, rs617135, rs618499, rs622920, rs624761, rs627178, rs641118, rs642612, rs6430090, rs6451453, rs6458458, rs6473080, rs6479916, rs6498220, rs650943, rs6512077, rs6535872, rs6542225, rs6546889, rs6551575, rs655231, rs65552910, rs6555483, rs6557512, rs65562177, rs65569979, rs6577561, rs6577853, rs6591559, rs6594842, rs6603530, rs6603781, rs6621070, rs6631389, rs6632813, rs6636980, rs6654877, rs6658884, rs6675497, rs6677009, rs667897, rs6683441, rs6689572, rs670139, rs6705923, rs6706570, rs6709683, rs6716363, rs6724143, rs6726524, rs6729547, rs673281, rs6749325, rs676309, rs6770617, rs6796090, rs6800578, rs6800857, rs6817424, rs6828228, rs685859, rs6861510, rs6865969, rs6869793, rs687582, rs6903671, rs6914564, rs6966132, rs6983226, rs6997082, rs7001207, rs7018666, rs7018692, rs7018850, rs7026025, rs7031164, rs7031458, rs703374, rs7040120, rs7044778, rs7051342, rs7061770, rs7064361, rs7069106, rs7070647, rs7071432, rs7076076, rs7082405, rs7084466, rs7084673, rs7086393, rs7106518, rs7108663, rs7120207, rs7123220, rs713952, rs714235, rs7148564, rs7152695, rs7161372, rs7164426, rs717666, rs718376, rs7190355, rs7196364, rs7197825, rs7199809, rs7203844, rs7207413, rs7210605, rs7212136, rs7215182, rs7220146, rs7225545, rs7243684, rs7243917, rs7249558, rs7250661, rs7254358, rs7290458, rs7294982, rs7297136, rs7298828, rs7316571, rs7319447, rs7322229, rs7365975, rs738977, rs7423892, rs7495307, rs7499241, rs7517009, rs7517283, rs7532358, rs7535789, rs7577837, rs7579138, rs7580100, rs759112, rs7595401, rs7603548, rs7606424, rs7615639, rs7625628, rs7648664, rs7666693, rs7674035, rs7679858, rs7694032, rs7699718, rs7702491, rs7722665, rs7726558, rs7734932, rs7737490, rs7753479, rs7773435, rs7821916, rs7824527, rs7825534, rs783376, rs7846493, rs7849193, rs7856017, rs7868954, rs7869556, rs7871777, rs7872516, rs7876084, rs7878331, rs7895861, rs7896662, rs7908601, rs7947761, rs7955859, rs7998410, rs8006542, rs8014761, rs8015610, rs802441, rs802466, rs8042680, rs805530, rs805531, rs8057620, rs8070132, rs8082463, rs8082787, rs8110666, rs8112746, rs8129151, rs820255, rs824631, rs829465, rs829467, rs831480, rs846814, rs846818, rs846825, rs847386, rs848492, rs853389, rs853585, rs865671, rs880293, rs884771, rs890731, rs891088, rs914593, rs9267135, rs9285657, rs9291171, rs9309095, rs9324521, rs9329143, rs9332441, rs9351848, rs9369572, rs9374351, rs9375555, rs9376083, rs9378774, rs9390645, rs9394781, rs9395110, rs9405199, rs9424093, rs9427206, rs942950, rs943218, rs9434717, rs9435127, rs9472557, rs9485905, rs9494139, rs949973, rs950027, rs9504837, rs9520114, rs953362, rs953363, rs9544313, rs9555552, rs957979, rs958935, rs9635948, rs9651104, rs9651363, rs9652690, rs9652691, rs9654458, rs9706460, rs971354, rs9776031, rs9780606, rs9784631, rs9807618, rs980793, rs9812119, rs9812150, rs9842566, rs9872847, rs9889183, rs9896422, rs9898218, rs9899379, rs9904820, rs9909601, rs991110, rs9914336, rs9931815, rs9964709, rs999939, and rs9999758;

detecting a second marker consisting of an E3 allele of APOE;

classifying the subject into a risk group based upon the presence or absence of the markers; and wherein detection of the first marker is provided by a first probe and detection of the second marker is provided by a second probe, and further wherein the first probe and the second probe are affixed to a solid support of a microarray.

2. The method of claim 1, further comprising isolating nucleic acid from the sample.

3. The method of claim 1, wherein the markers are detected directly.

4. The method of claim 3, wherein the detecting the markers further comprises a method selected from the group consisting of microarray analysis of genomic DNA with a gene chip and comparative genomic hybridization.

5. The method of claim 1, wherein the markers are associated with a low risk of developing LOAD and the subject is classified to a risk group with low risk of LOAD if the marker is detected in the sample.

6. The method of claim 5, wherein the first marker is the A allele of rs17042395.

7. The method of claim 6, wherein the subject is further classified based on the presence of two copies of the APOE-e3 allele.

8. A set of molecular probes used in assessing the risk of developing late onset Alzheimer's disease (LOAD) comprising:

a first probe capable of detecting a first SNP selected from a group consisting of rs10009946, rs1002261, rs10031360, rs10036338, rs10037238, rs10040520, rs10051640, rs10054011, rs10062543, rs10066153, rs10069118, rs10069190, rs10077548, rs10079121, rs1008055, rs1009940, rs1009947, rs1009987, rs10110144, rs10115578, rs10121466, rs10140673, rs10188267, rs10192963, rs10194172, rs10194269, rs1019670, rs10198042, rs10198317, rs10199416, rs1021632, rs10231253, rs1023964, rs10253781, rs1026254, rs1026255, rs10267678, rs1039147, rs10400909, rs1040211, rs10402271, rs10426094, rs10430148, rs10448254, rs10454797, rs10476994, rs10477463, rs10482042, rs10503040, rs10504376, rs10504377, rs10511964, rs10512156, rs10514883, rs10515026, rs10515029, rs10515386, rs10519170, rs1060455, rs10733121, rs10741175, rs10742719, rs10742722, rs10742725, rs10747215, rs10758596, rs10758597, rs10773829, rs10773890, rs10777410, rs10783282, rs10787629, rs1079022, rs10790519, rs10792084, rs10792267, rs10799801, rs10814235, rs1081900, rs10819162, rs10819173, rs10819174, rs10820403, rs10825816, rs10825817, rs10848219, rs10859338, rs10866514, rs10869422, rs10878636, rs10885864, rs10892873, rs10897003, rs10897020, rs10897049, rs10900908, rs10915495, rs10945913, rs10950253, rs10950254, rs10974449, rs10974859, rs10988348, rs11016132, rs1102617, rs11038193, rs11049049, rs11066247, rs11073964, rs11079804, rs1108209, rs11092309, rs11095608, rs11097396, rs1109916, rs11106228, rs11106700, rs1111218, rs11114028, rs11133030, rs11133248, rs11133602, rs11133822, rs11143837, rs11150971, rs11159907, rs11170973, rs11180553, rs11217627, rs11218016, rs11229192, rs11230180, rs1123024, rs11237698, rs11239751, rs11241620, rs1124165, rs1124166, rs11257695, rs11266413, rs1130371, rs11149736, rs1155098, rs11584403, rs1160985, rs11629688, rs11646101, rs11647759, rs11655913, rs11671804, rs11676819, rs11691971, rs11694165, rs11698059, rs11710973, rs11738432, rs11741205, rs11748700, rs11752453, rs11778430, rs1178520, rs11788891, rs1181913, rs1184766, rs11858967, rs11861905, rs11872966, rs11889938, rs11914999, rs11947861, rs11954932, rs12006950, rs12009590, rs1202525, rs12037204, rs12037869, rs1204331, rs12084240, rs12107500, rs12123186, rs12127313, rs12186632, rs12191684, rs12196957, rs12225299, rs12238307, rs12265862, rs12294703, rs12313149, rs12316258, rs12318549, rs12326462, rs1233078, rs12336107, rs12342299, rs12375106, rs12395571, rs12408105, rs12440774, rs12444393, rs12446552, rs12468287, rs12495316, rs12499442, rs12511743, rs12513052, rs12539316, rs12555462, rs1256424, rs1256428, rs1256444, rs1256447, rs12595616, rs12598082, rs12601300, rs12606449, rs12617390, rs12628020, rs12632665, rs12632797, rs12647148, rs12648659, rs12652190, rs12658719, rs12659288, rs12685147, rs12686342, rs12692593, rs12723357, rs12741415, rs12749061, rs1277307, rs12781952, rs12798784, rs12800777, rs12809801, rs12818087, rs12829992, rs1284059, rs12892914, rs12909713, rs12910825, rs12922082, rs12969851, rs13013898, rs13020250, rs13029092, rs13033552, rs13037545, rs13053558, rs13068144, rs13302146, rs13313001, rs1332249, rs13381188, rs13382950, rs13395944, rs13404031, rs13417560, rs1346440, rs1350089, rs1352576, rs1359651, rs1362729, rs1366413, rs1372254, rs1372567, rs1377334, rs1378169, rs1393360, rs1395773, rs1409427, rs1409428, rs1416770, rs1417032, rs1442063, rs1453013, rs1460191, rs1467737, rs1471994, rs1478281, rs1479560, rs1479831, rs1511556, rs1519812, rs1523314, rs1530914, rs1531347, rs1533822, rs1537989, rs1540125, rs1547329, rs1553497, rs1566106, rs1566430, rs158134, rs1582763, rs1596039, rs1604382, rs1618513, rs1634507, rs1634508, rs167602, rs16830888, rs16834130, rs16841583, rs16852038, rs16852953, rs16854702, rs1685513, rs16857593, rs16863859, rs16863867, rs16864008, rs16879230, rs16879693, rs16889006, rs16900667, rs16901211, rs16914456, rs16918465, rs16931253, rs16931257, rs16931273, rs16943700, rs16950383, rs16951392, rs16959238, rs16964797, rs16971511, rs16979301, rs16983551, rs16995332, rs17016207, rs17025061, rs17034079, rs17039828, rs17042395, rs17048072, rs17056952, rs17087898, rs17091212, rs17091253, rs17091265, rs17095426, rs17095429, rs17098400, rs17105491, rs17117632, rs17133758, rs17135372, rs17137349, rs17145817, rs1719141, rs1719210, rs1719220, rs17207648, rs17236661, rs17237607, rs17253937, rs17255138, rs17317101, rs17332633, rs17383755, rs17410182, rs17431, rs17465431, rs17488034, rs17494056, rs17498815, rs17522996, rs1752653, rs17594509, rs17598123, rs17599877, rs17600575, rs17602572, rs17643262, rs17650435, rs17654608, rs17711743, rs17712565, rs1772988, rs17734389, rs17771318, rs17773314, rs1778596, rs17797399, rs17835266, rs17835397, rs17865911, rs1798021, rs1805952, rs1805957, rs1805960, rs182174, rs1823667, rs1869620, rs1879818, rs1881441, rs1882569, rs1883487, rs1883488, rs1918676, rs1939184, rs1939194, rs1943229, rs1943783, rs1945390, rs1954850, rs1959185, rs1966374, rs1993471, rs1997608, rs2001217, rs2001517, rs200545, rs200547, rs2017823, rs2019707, rs2025466, rs202869, rs2031183, rs2033494, rs2034085, rs2040507, rs2042922, rs2043422, rs2057915, rs2058810, rs2059129, rs2062368, rs2081547, rs2090922, rs2110641, rs2110706, rs2127470, rs2131361, rs2136342, rs2136343, rs2139109, rs2139615, rs2152649, rs2160491, rs2166500, rs217034, rs2181987, rs2203432, rs2204608, rs2213369, rs2224182, rs2232313, rs2234246, rs2242945, rs2250392, rs2252238, rs2267346, rs227103, rs2273235, rs2277365, rs2278583, rs2286276, rs2288522, rs2289711, rs2304935, rs2317481, rs2346709, rs2356132, rs236573, rs2382492, rs2398485, rs2398671, rs2402961, rs2415025, rs2430373, rs2437801, rs2437803, rs2447265, rs2455787, rs2462645, rs2479505, rs2486027, rs2486866, rs2495988, rs2500144, rs2500153, rs2503285, rs252272, rs252950, rs252977, rs2541286, rs2544081, rs2577894, rs2593529, rs2594953, rs2603779, rs2612589, rs2612600, rs2624938, rs2635296, rs264256, rs2649627, rs2653322, rs2694814, rs2712590, rs2728524, rs275467, rs2809591, rs2812237, rs2819190, rs2827879, rs2827881, rs2827882, rs2827909, rs2827911, rs2833325, rs2834330, rs2834341, rs2834344, rs2837995, rs28515995, rs2856044, rs2879724, rs2880301, rs2881458, rs2881599, rs2885856, rs2898441, rs2899683, rs2900285, rs2901098, rs293540, rs293541, rs293542, rs293545, rs2954892, rs2956581, rs2960455, rs298069, rs298185, rs2997967, rs3019879, rs3104993, rs3104996, rs3112160, rs3118077, rs3120733, rs3127080, rs319855, rs319858, rs3208856, rs321325, rs32425, rs3323, rs34661737, rs35306465, rs35393495, rs35762589, rs35775016, rs371298, rs3745546, rs3755311, rs3768235, rs3777530, rs3781533, rs3786954, rs3790971, rs379717, rs3813097, rs3814127, rs3822459, rs3828191, rs3829304, rs3886569, rs3912944, rs3913840, rs394457, rs3960965, rs397118, rs40353, rs40665, rs40666, rs4072688, rs4090174, rs4097545, rs4113946, rs4121392, rs41323947, rs41381844, rs41390747, rs41407844, rs41437548, rs41447448, rs4147047, rs4233036, rs4237493, rs4241009, rs42495, rs4257715, rs4272222, rs4283782, rs4286782, rs4289558, rs4306376, rs4307374, rs4315367, rs4316805, rs4336923, rs4342343, rs4354335, rs4357331, rs4362707, rs4369216, rs4382847, rs4384677, rs4393536, rs4410671, rs4420638, rs4421130, rs4479297, rs4487976, rs4506675, rs4510072, rs4514520, rs4533297, rs4537793, rs4547126, rs4555926, rs4562978, rs456298, rs4576739, rs4639843, rs4643583, rs4648858, rs4648959, rs4652931, rs466093, rs4676320, rs4694116, rs4695895, rs4699882, rs4701641, rs4701734, rs4743641, rs4744768, rs4746100, rs4771531, rs4793734, rs4794225, rs4794346, rs4794347, rs4813394, rs4821990, rs4827479, rs4829946, rs4842993, rs4843267, rs4844600, rs4861498, rs4861864, rs4862558, rs4864737, rs4875330, rs4898337, rs4898872, rs4903240, rs4903243, rs4910821, rs4921744, rs492496, rs4938931, rs4953706, rs4955753, rs4956509, rs4961257, rs4961341, rs4964586, rs4972391, rs4975725, rs4978968, rs4978970, rs4984259, rs5015994, rs508915, rs541965, rs552409, rs558514, rs559664, rs562028, rs5756261, rs5758223, rs5758267, rs5763001, rs589605, rs5907046, rs5910606, rs5910607, rs5910608, rs5935673, rs5945088, rs5951325, rs5955490, rs5956359, rs5962536, rs5964670, rs5966049, rs5978287, rs5981380, rs5981711, rs5987025, rs5991907, rs5992600, rs6022638, rs6039654, rs6075709, rs6082159, rs6094509, rs610352, rs6123167, rs6137147, rs614013, rs617135, rs618499, rs622920, rs624761, rs627178, rs641118, rs642612, rs6430090, rs6451453, rs6458458, rs6473080, rs6479916, rs6498220, rs650943, rs6512077, rs6535872, rs6542225, rs6546889, rs6551575, rs655231, rs6552910, rs6555483, rs6557512, rs6562177, rs6569979, rs6577561, rs6577853, rs6591559, rs6594842, rs6603530, rs6603781, rs6621070, rs6631389, rs6632813, rs6636980, rs6654877, rs6658884, rs6675497, rs6677009, rs667897, rs6683441, rs6689572, rs670139, rs6705923, rs6706570, rs6709683, rs6716363, rs6724143, rs6726524, rs6729547, rs673281, rs6749325, rs676309, rs6770617, rs6796090, rs6800578, rs6800857, rs6817424, rs6828228, rs685859, rs6861510, rs6865969, rs6869793, rs687582, rs6903671, rs6914564, rs6966132, rs6983226, rs6997082, rs7001207, rs7018666, rs7018692, rs7018850, rs7026025, rs7031164, rs7031458, rs703374, rs7040120, rs7044778, rs7051342, rs7061770, rs7064361, rs7069106, rs7070647, rs7071432, rs7076076, rs7082405, rs7084466, rs7084673, rs7086393, rs7106518, rs7108663, rs7120207, rs7123220, rs713952, rs714235, rs7148564, rs7152695, rs7161372, rs7164426, rs717666, rs718376, rs7190355, rs7196364, rs7197825, rs7199809, rs7203844, rs7207413, rs7210605, rs7212136, rs7215182, rs7220146, rs7225545, rs7243684, rs7243917, rs7249558, rs7250661, rs7254358, rs7290458, rs7294982, rs7297136, rs7298828, rs7316571, rs7319447, rs7322229, rs7365975, rs738977, rs7423892, rs7495307, rs7499241, rs7517009, rs7517283, rs7532358, rs7535789, rs7577837, rs7579138, rs7580100, rs759112, rs7595401, rs7603548, rs7606424, rs7615639, rs7625628, rs7648664, rs7666693, rs7674035, rs7679858, rs7694032, rs7699718, rs7702491, rs7722665, rs7726558, rs7734932, rs7737490, rs7753479, rs7773435, rs7821916, rs7824527, rs7825534, rs783376, rs7846493, rs7849193, rs7856017, rs7868954, rs7869556, rs7871777, rs7872516, rs7876084, rs7878331, rs7895861, rs7896662, rs7908601, rs7947761, rs7955859, rs7998410, rs8006542, rs8014761, rs8015610, rs802441, rs802466, rs8042680, rs805530, rs805531, rs8057620, rs8070132, rs8082463, rs8082787, rs8110666, rs8112746, rs8129151, rs820255, rs824631, rs829465, rs829467, rs831480, rs846814, rs846818, rs846825, rs847386, rs848492, rs853389, rs853585, rs865671, rs880293, rs884771, rs890731, rs891088, rs914593, rs9267135, rs9285657, rs9291171, rs9309095, rs9324521, rs9329143, rs9332441, rs9351848, rs9369572, rs9374351, rs9375555, rs9376083, rs9378774, rs9390645, rs9394781, rs9395110, rs9405199, rs9424093, rs9427206, rs942950, rs943218, rs9434717, rs9435127, rs9472557, rs9485905, rs9494139, rs949973, rs950027, rs9504837, rs9520114, rs953362, rs953363, rs9544313, rs9555552, rs957979, rs958935, rs9635948, rs9651104, rs9651363, rs9652690, rs9652691, rs9654458, rs9706460, rs971354, rs9776031, rs9780606, rs9784631, rs9807618, rs980793, rs9812119, rs9812150, rs9842566, rs9872847, rs9889183, rs9896422, rs9898218, rs9899379, rs9904820, rs9909601, rs991110, rs9914336, rs9931815, rs9964709, rs999939, and rs9999758; and a second probe capable of detecting an E3 allele of APOE; wherein the probes are affixed to a solid support of a microarray.

9. The set of claim 8, wherein the first probe is capable of detecting a SNP associated with a higher risk of LOAD.

10. The set of claim 9, wherein the second probe is capable of detecting a SNP associated with a lower risk of developing LOAD.

11. The set of claim 8, wherein the first probe and the second probe are capable of detecting a SNP associated with a lower risk of developing LOAD.

12. A set of molecular probes used in assessing the risk of developing late onset Alzheimer's disease (LOAD) comprising:
a first probe for detecting an A allele of rs17042395, wherein a first label is coupled to the first probe; and
a second probe for detecting an E3 allele of APOE wherein a second label is coupled to the second probe;
wherein the presence of both the A allele of rs17042395 and the E3 allele of APOE is associated with a lower risk of developing LOAD, and further wherein the first label and the second label are selected from the group consisting of a radioactive isotope or chelate thereof, a fluorescent dye, a non-fluorescent dye, a stain, an enzyme, a metal, or combinations thereof.

13. A method of classifying a subject to a late onset Alzheimer's disease (LOAD) risk group, comprising:
receiving a sample from the subject;
detecting a first marker consisting of an A allele of rs17042395;
detecting a second marker consisting of an E3 allele of APOE;
classifying the subject in a low LOAD risk group if both the A allele of rs17042395 and the E3 allele of APOE are detected; and
wherein detection of the first marker is provided by a first probe and detection of the second marker is provided by a second probe, the first probe being coupled to a first label and the second probe being coupled to a second label, and further wherein the first label and the second label are selected from the group consisting of a radioactive isotope or chelate thereof, a fluorescent dye, a non-fluorescent dye, a stain, an enzyme, a metal, or combinations thereof.

14. The method of claim 13, further comprising isolating nucleic acid from the sample.

15. The method of claim 13, wherein the first and second markers are detected directly.

16. The method of claim 15, wherein the detecting the markers further comprises a method selected from the group consisting of Sanger sequencing, pyrosequencing, SOLID sequencing, massively parallel sequencing, barcoded DNA sequencing, PCR, real-time PCR, quantitative PCR, microarray analysis of genomic DNA with a gene chip, restriction fragment length polymorphism analysis, allele specific ligation, and comparative genomic hybridization.

17. The method of claim 13, wherein the first and second markers are detected indirectly.

18. The method of claim 17, wherein detecting the markers further comprises a method selected from the group consisting of microarray analysis of RNA, RNA in situ hybridization, RNAse protection assay, Northern blot, reverse transcriptase PCR, quantitative PCR, quantitative reverse transcriptase PCR, quantitative real-time reverse transcriptase PCR, reverse transcriptase treatment followed by direct sequencing, flow cytometry, immunohistochemistry, ELISA, Western blot, immunoaffinity chromatography, HPLC, mass spectrometry, protein microarray analysis, PAGE analysis, isoelectric focusing, and 2-D gel electrophoresis.

19. The set of claim 8, wherein the first probe detects an A allele of rs17042395.

\* \* \* \* \*